US008133238B2

(12) United States Patent
Maruyama et al.

(10) Patent No.: US 8,133,238 B2
(45) Date of Patent: Mar. 13, 2012

(54) TISSUE CLOSING DEVICE

(75) Inventors: Tomoji Maruyama, Kanagawa (JP); Masakatsu Kawaura, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1610 days.

(21) Appl. No.: 11/434,925

(22) Filed: May 17, 2006

(65) Prior Publication Data
US 2006/0265008 A1 Nov. 23, 2006

(30) Foreign Application Priority Data

May 18, 2005 (JP) ................. 2005-146076

(51) Int. Cl.
*A61B 17/04* (2006.01)
(52) U.S. Cl. ......... 606/139; 606/232; 606/213; 606/142
(58) Field of Classification Search .................. 606/74, 606/103, 139, 144–148, 213, 232–233
See application file for complete search history.

(56) References Cited

U.S. PATENT DOCUMENTS

| | | | | | |
|---|---|---|---|---|---|
| 4,917,089 | A | * | 4/1990 | Sideris | 606/215 |
| 5,021,059 | A | * | 6/1991 | Kensey et al. | 606/213 |
| 5,290,310 | A | * | 3/1994 | Makower et al. | 606/213 |
| 5,411,520 | A | * | 5/1995 | Nash et al. | 606/213 |
| 5,549,633 | A | * | 8/1996 | Evans et al. | 606/139 |
| 5,931,844 | A | * | 8/1999 | Thompson et al. | 606/144 |
| 5,935,147 | A | * | 8/1999 | Kensey et al. | 606/213 |
| 6,312,446 | B1 | * | 11/2001 | Huebsch et al. | 606/213 |
| 6,500,184 | B1 | * | 12/2002 | Chan et al. | 606/144 |
| 6,551,344 | B2 | * | 4/2003 | Thill | 606/213 |
| 6,860,895 | B1 | * | 3/2005 | Akerfeldt et al. | 606/215 |
| 7,311,720 | B2 | * | 12/2007 | Mueller et al. | 606/213 |
| 7,837,705 | B2 | * | 11/2010 | White et al. | 606/213 |
| 2003/0199923 | A1 | * | 10/2003 | Khairkhahan et al. | 606/213 |

FOREIGN PATENT DOCUMENTS

| | | |
|---|---|---|
| EP | 0 534 696 A1 | 3/1993 |
| JP | 5-212038 | 8/1993 |
| JP | 3133059 | 11/2000 |
| WO | WO 9310714 A1 * | 6/1993 |
| WO | WO 00/78226 * | 6/1999 |

* cited by examiner

*Primary Examiner* — Darwin Erezo
*Assistant Examiner* — Mark Mashack
(74) *Attorney, Agent, or Firm* — Buchanan Ingersoll & Rooney PC

(57) ABSTRACT

A tissue closing device includes an elongate arrangement device of which a distal end portion can penetrate an opening on a wall of living body cavity and which has a hand-operated portion on the proximal side, and a closure detachably retained at the distal end portion of the arrangement device and operative to close the opening. According to one embodiment, the arrangement device can include a thread for detachably retaining the closure and for pulling the closure in the proximal direction, a cover tube, and a fixed tube. The hand-operated portion has a canceling mechanism for canceling the retained state of the closure. A series of operations from deformation of the closure resulting from pulling the closure by the thread to canceling the retained state of the closure by the canceling mechanism after completion of the deformation are performed continuously by operating the hand-operated portion.

27 Claims, 23 Drawing Sheets

TISSUE CLOSING DEVICE

FIELD OF THE INVENTION

The present invention relates to a device typically used in a medical procedure. More particularly, the invention pertains to a tissue closing device.

BACKGROUND DISCUSSION

Low-invasion operations carried out by inserting a device for diagnosis or treatment, such as a catheter, into a blood vessel or some other tissue are known and performed on a quite often basis. For example, to treat a constriction of the coronary artery of the heart, it is necessary to insert a device such as a catheter into a blood vessel in order to perform therapeutic treatment on the constriction.

This insertion of an instrument such as a catheter into a blood vessel is normally performed through a puncture formed by dissecting or puncturing the femoral region. After the therapeutic treatment is completed, it is necessary to perform a staunching operation to stop the bleeding through the puncture. However, since the blood pressure upon bleeding (bleeding blood pressure) from the femoral artery is relatively high, it is oftentimes necessary for a person involved in the medical procedure to use a finger of their hand to press down on the site for a relatively long period of time.

In recent years, to perform the stoppage of bleeding more readily and with greater certainty, a variety of devices have been proposed for insertion through an opening penetrating a tissue membrane (an opening on a wall of living body cavity) to close the opening (e.g., the opening in the blood vessel). The device disclosed in Japanese Patent No. 3133059, (corresponding to U.S. Pat. No. 5,593,422) is an example.

Japanese Patent No. 3133059 discloses a device in which a closing member with a thread attached thereto is disposed in a blood vessel, a ring (locking member) is moved along the thread, and the ring locks the thread outside the blood vessel to close up the opening formed in the wall of the blood vessel.

In this disclosed device, the closing member is secured to the wall of the blood vessel by fixing the ring to the thread.

However, with the device just mentioned, since the fixing operation involving the fixing of the ring to the thread must be performed within subcutaneous tissues, the fixing operation is difficult to carry out. Besides, after the ring is fixed to the thread, it is necessary to cut the thread within the subcutaneous tissues. Therefore, labor, time and skill are required to close up the opening formed in the wall of the blood vessel.

Further, since the outside diameter of the ring needs to be dimensioned so that the ring can be inserted into the opening, the ring must necessarily be relatively small in size, and there is the possibility that the ring may drop into the blood vessel through the opening formed in the wall of the blood vessel.

SUMMARY

A tissue closing device for closing an opening penetrating a living tissue comprises a closure for closing the opening in the living tissue, wherein the closure comprises a seal portion adapted to cover the opening and a periphery of the opening from one side of the wall of the living body cavity, and a deformable deformation portion adapted to cover the opening and the periphery of the opening from an opposite side of the wall of the living body cavity. The tissue closure device also includes an arrangement device detachably retaining the closure to arrange the closure at a position to close the opening. The arrangement device comprises lock means for locking at least a part of the closure in a retained state, an operational portion provided on a proximal side of the lock means, and canceling means for canceling the retained state of the closure. The operational portion is operable to effect in a continuous operation relative movement between the closure and the lock means under a condition in which the closure is locked by the lock means to deform the deformation portion of the closure, and after completion of the deformation, to cancel the retained state of the closure by the canceling means.

According to another aspect, a tissue closing device for closing an opening penetrating living tissue comprises a closure adapted to close the opening and including a seal portion positionable on one side of the opening in the living tissue to cover the opening and a periphery of the opening and a deformable deformation portion positionable on an opposite side of the opening in the living tissue. The device also includes a body, an elongated tubular member extending distally of the body, a thread extending through the elongated tubular member and connected to the closure, a thread support portion movably positioned in the body and connected to the thread so that movement of the thread support portion moves the thread, and a manually operable operating lever mounted on the body and operatively connected to the thread support portion to move the thread support portion in a proximal direction away from the closure upon manual operation of the operating lever to move the thread in the proximal direction and apply a force to the closure which deforms the deformation portion so that the periphery of the opening penetrating the living tissue is positioned between the seal portion and the deformation portion which has been deformed.

According to a further aspect, a tissue closing device for closing an opening penetrating living tissue includes a closure adapted to close the opening and comprising a seal portion positionable on one side of the opening in the living tissue to cover the opening and a periphery of the opening and a deformable deformation portion positionable on an opposite side of the opening in the living tissue. The device also includes a body, an elongated tubular member extending distally of the body, a thread extending through the elongated tubular member and connected to the closure, a manually operable operating lever mounted on the body and operatively connected to the thread by a thread holder to move the thread in a proximal direction upon manual operation of the operating lever so that the thread applies a force to the closure which deforms the deformation portion so that the periphery of the opening penetrating the living tissue is positioned between the seal portion and the deformation portion which has been deformed, and a release member movably positioned in the body and engageable with the thread holder during manual operation of the operating lever to move the thread holder in a manner which releases the thread and operatively disconnects the thread and the operating lever.

In accordance with another aspect, a method of closing an opening penetrating living tissue involves positioning a closure relative to the opening so that a seal portion of the closure is positioned on one side of the opening in the living tissue to cover the opening and a periphery of the opening, and a deformable deformation portion of the closure is positioned on an opposite side of the opening in the living tissue, manually operating an operating lever to apply forces in opposite directions to the closure to deform the deformation portion to a deformed state in which the periphery of the opening penetrating the living tissue is positioned between the seal portion and the deformation portion which has been deformed, and continuing to manually operate the operating lever to release the forces.

In the tissue closing device, the living tissue (wall of a living body cavity) is preferably a wall of a blood vessel, and the one-side surface is the inside surface of the blood vessel wall.

BRIEF DESCRIPTION OF THE DRAWING FIGURES

Figure 1:
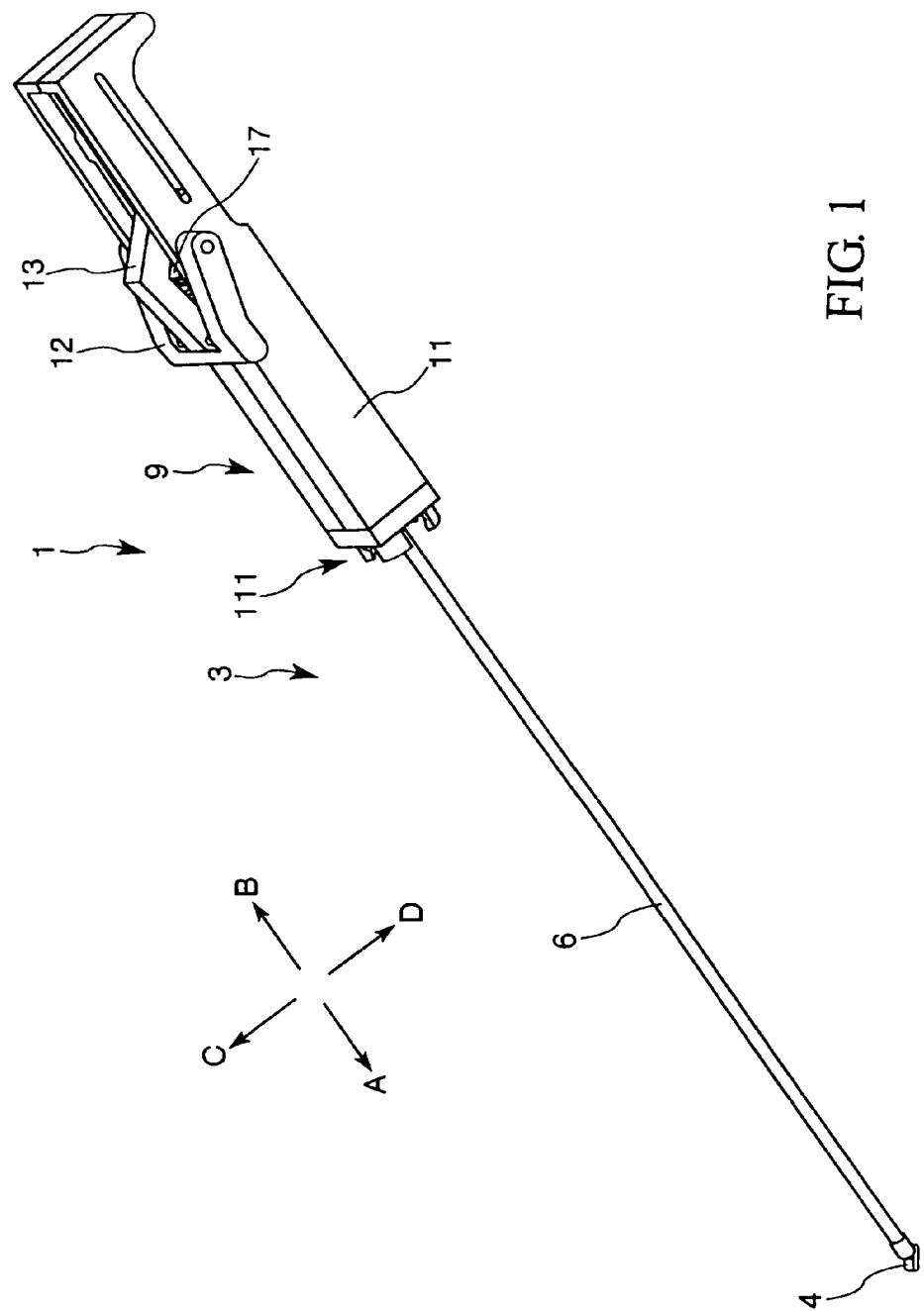
FIG. 1 is a perspective view of an embodiment of the tissue closing device disclosed herein.

FIGS. 11(a)-11(d) are perspective views of the clip used in the tissue closing device shown in FIG. 1 illustrating the clip in different forms of deformation.

Figure 12:
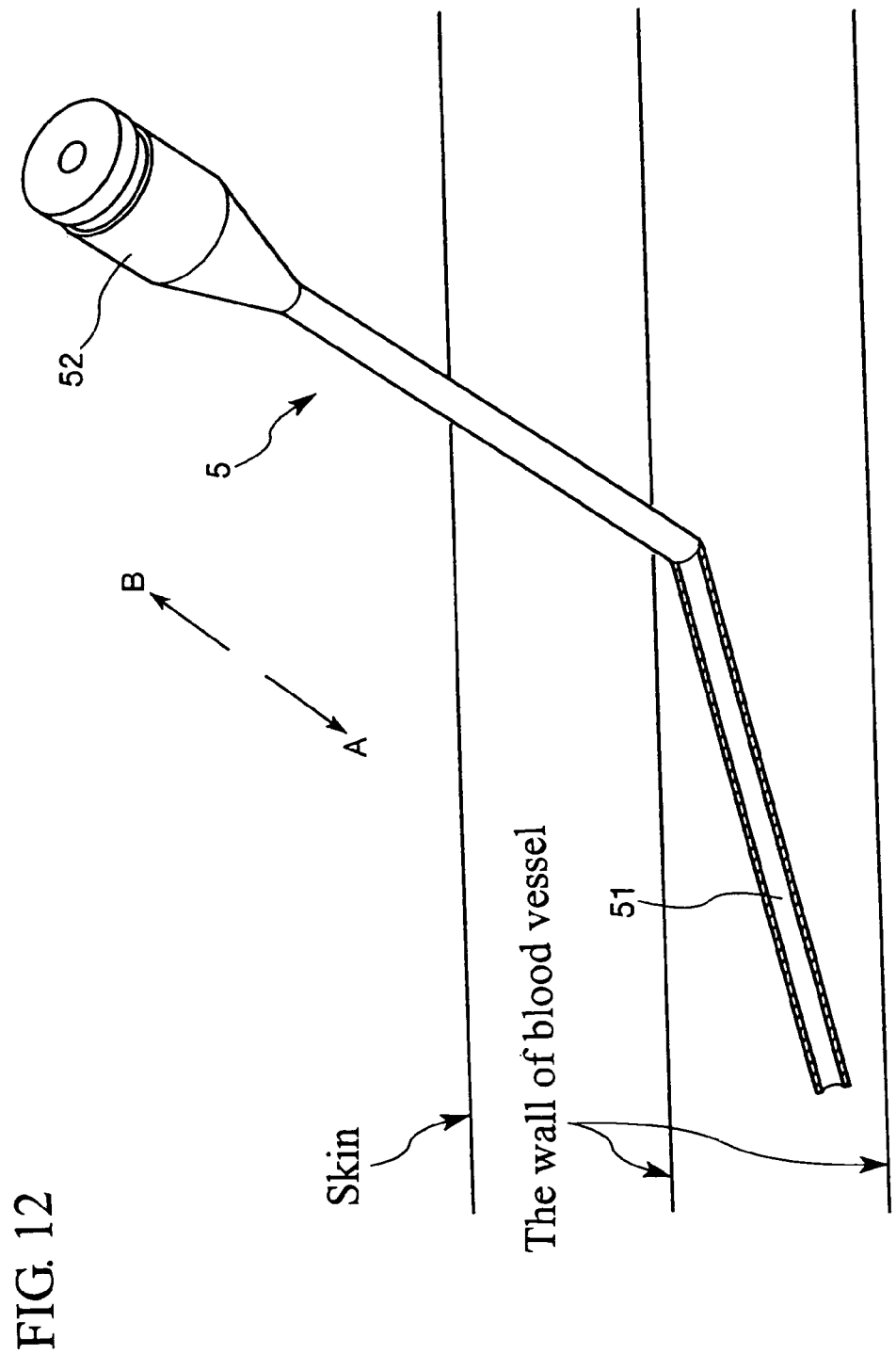

FIG. 12 is a perspective view of a sheath with which the tissue closing device shown in FIG. 1 can be used.

Figure 13:
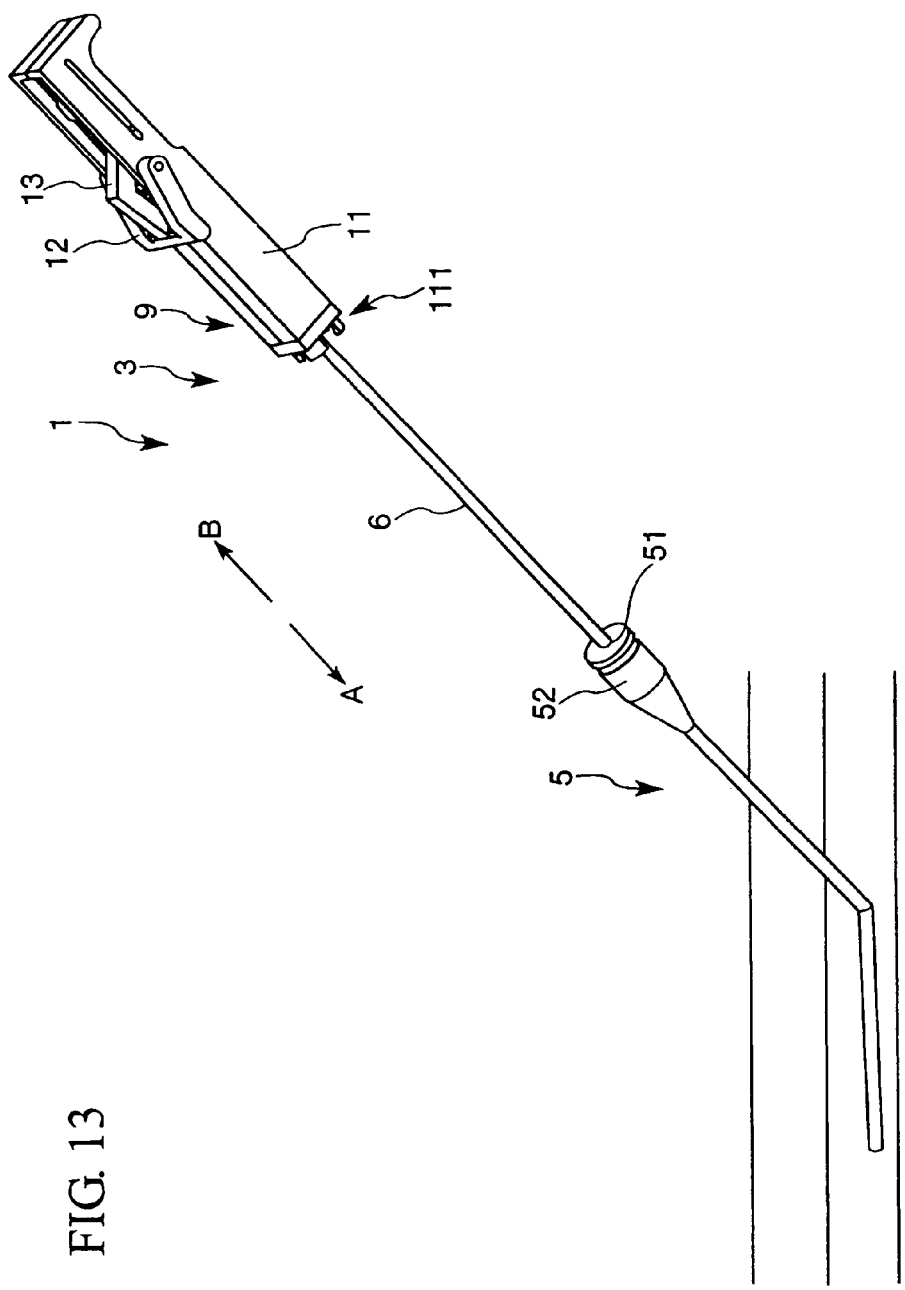

FIG. 13 is a perspective view of the tissue closing device shown in FIG. 1 being inserted into the sheath shown in FIG. 12.

Figure 14:
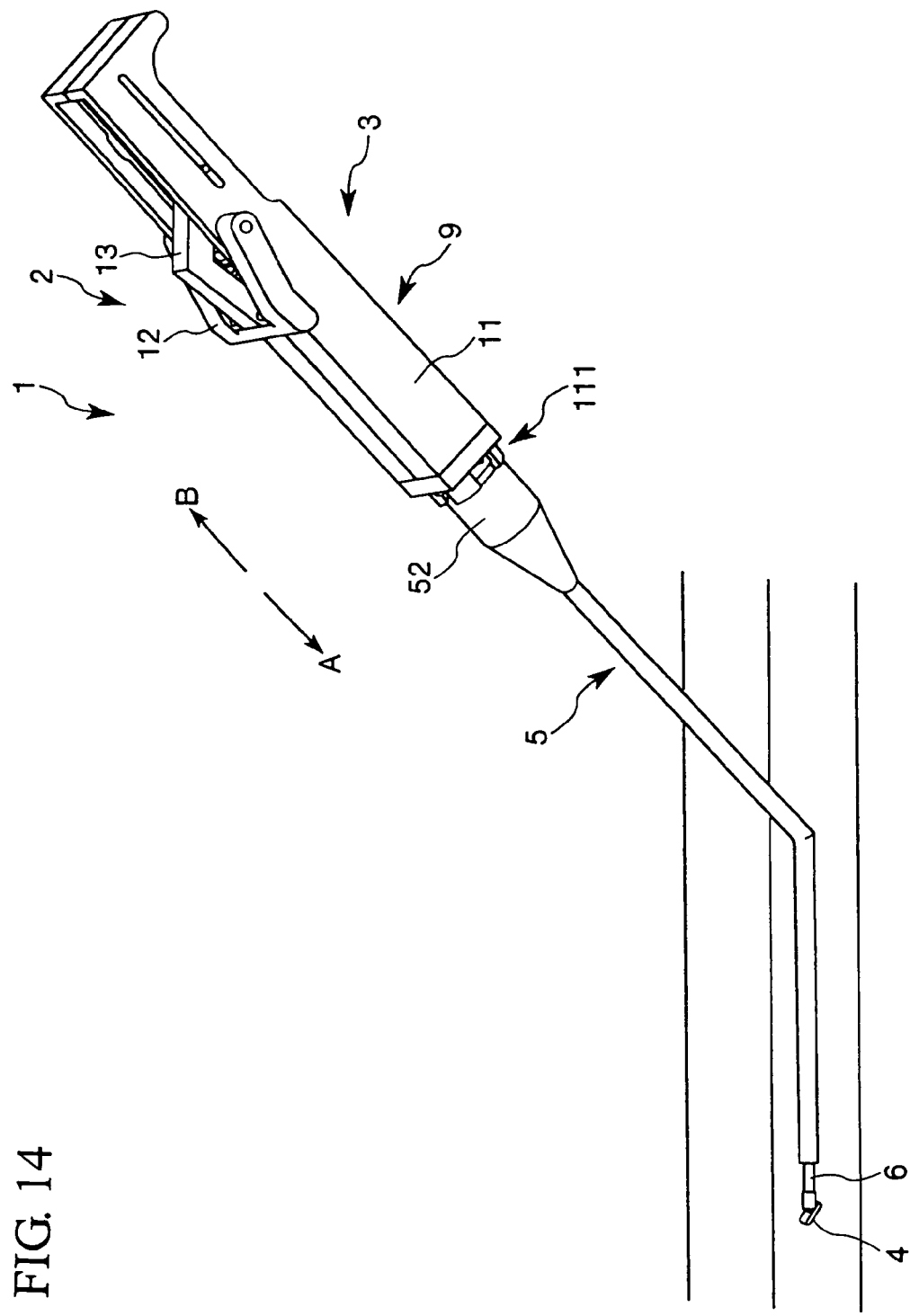

FIG. 14 is a perspective view of the tissue closing device shown in FIG. 1 after it is inserted into the sheath shown in FIG. 12.

Figure 15:
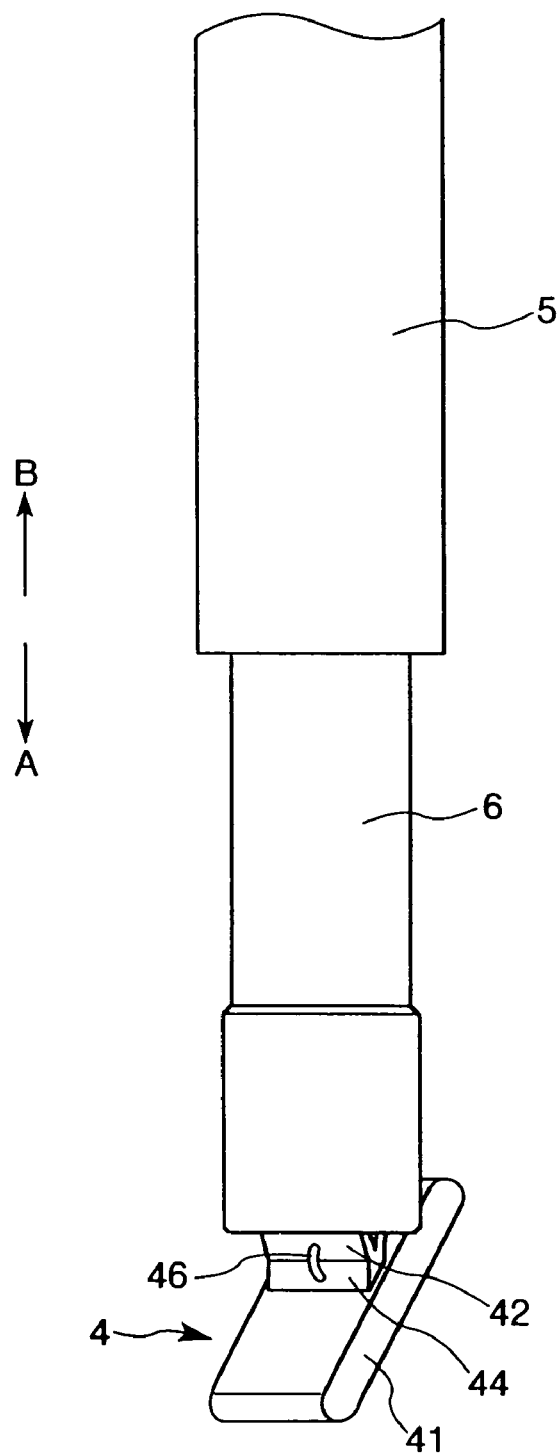

FIG. 15 is a perspective view of the distal end portion of the tissue closing device shown in FIG. 1 during use or operation.

Figure 16:
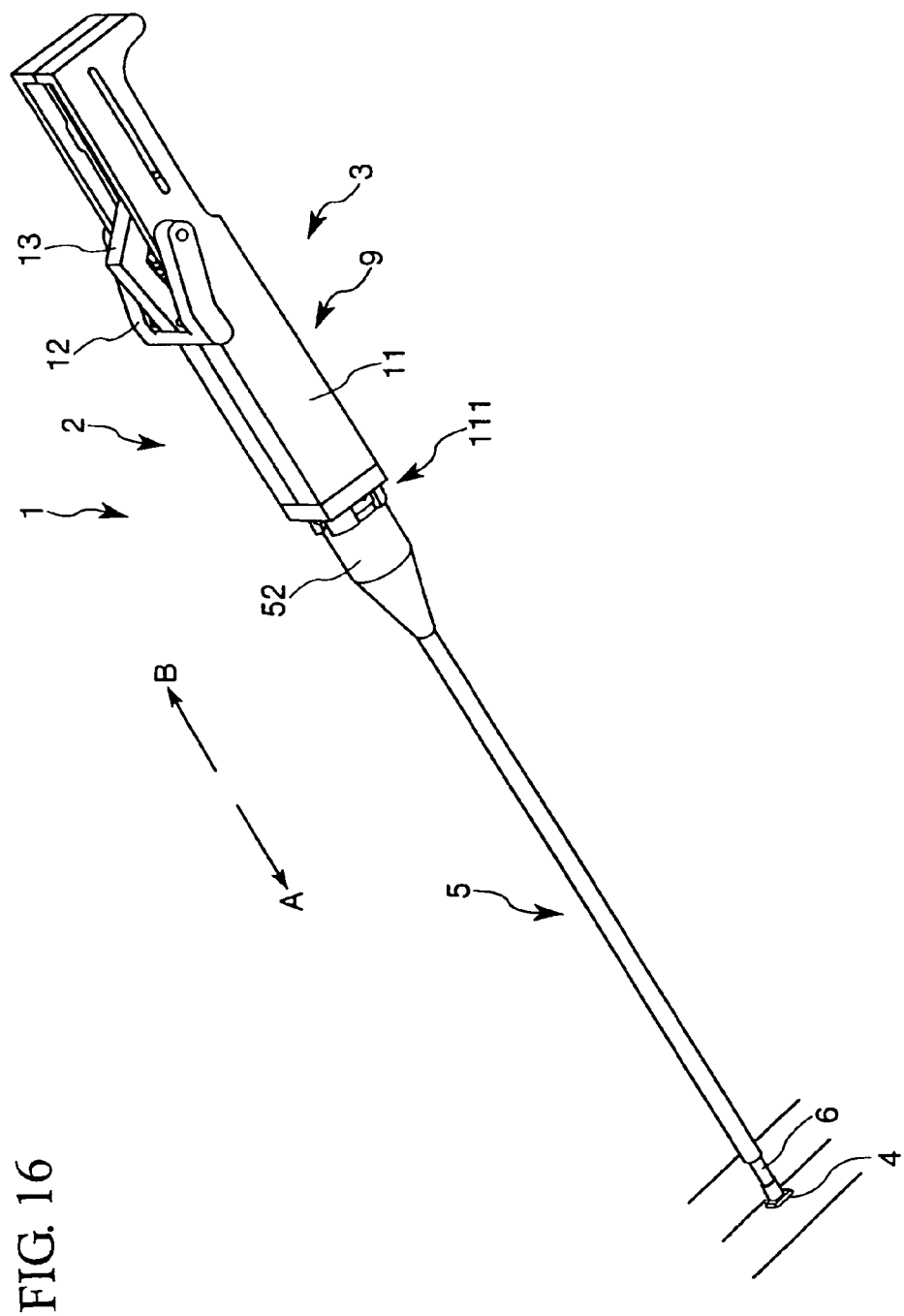

FIG. 16 is a perspective view of the tissue closing device shown in FIG. 1 inserted into the sheath shown in FIG. 12 during use or operation of the tissue closing device.

Figure 17:
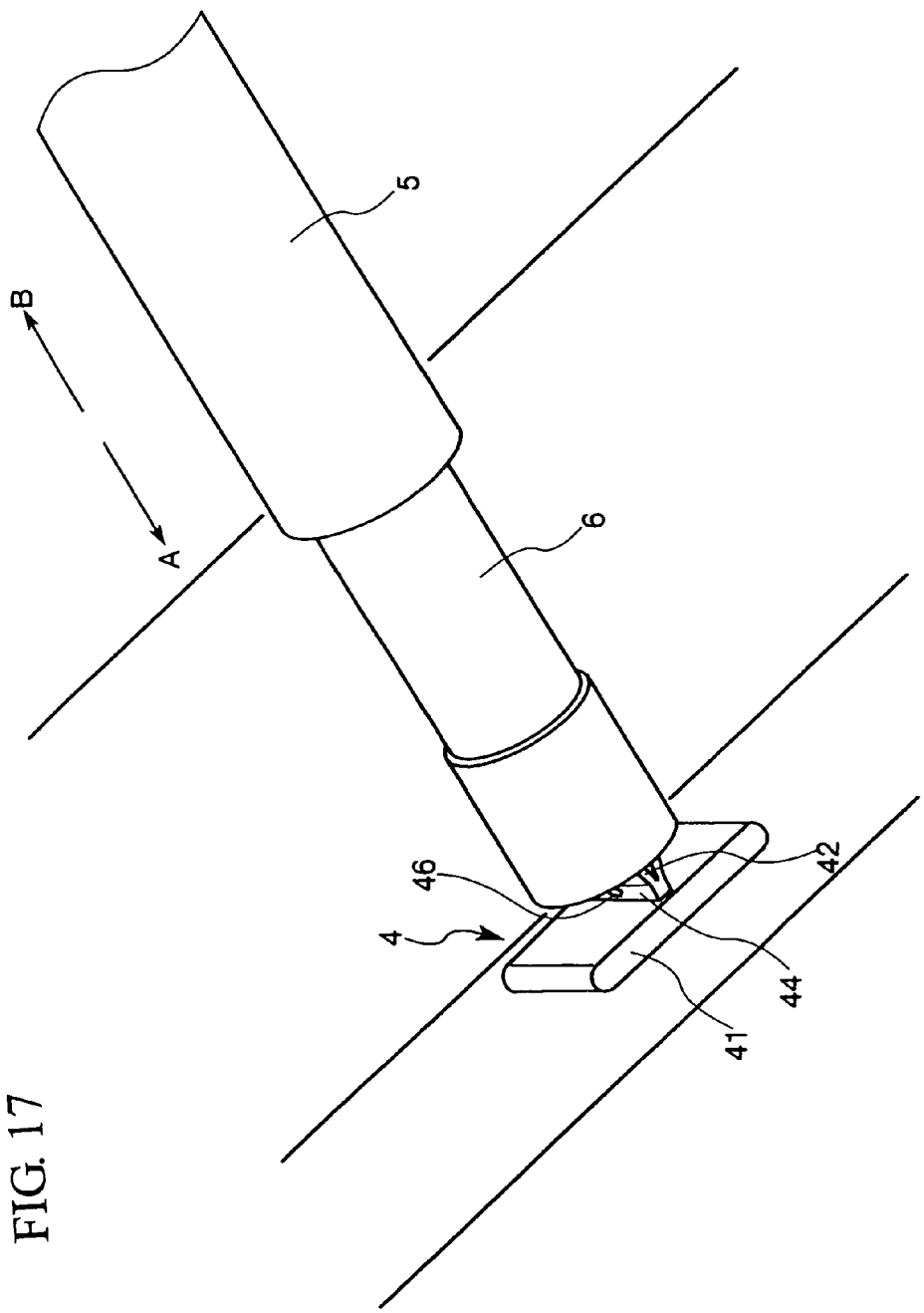

FIG. 17 is a perspective view illustrating an action (operation) of the tissue closing device shown in FIG. 1.

Figure 18:
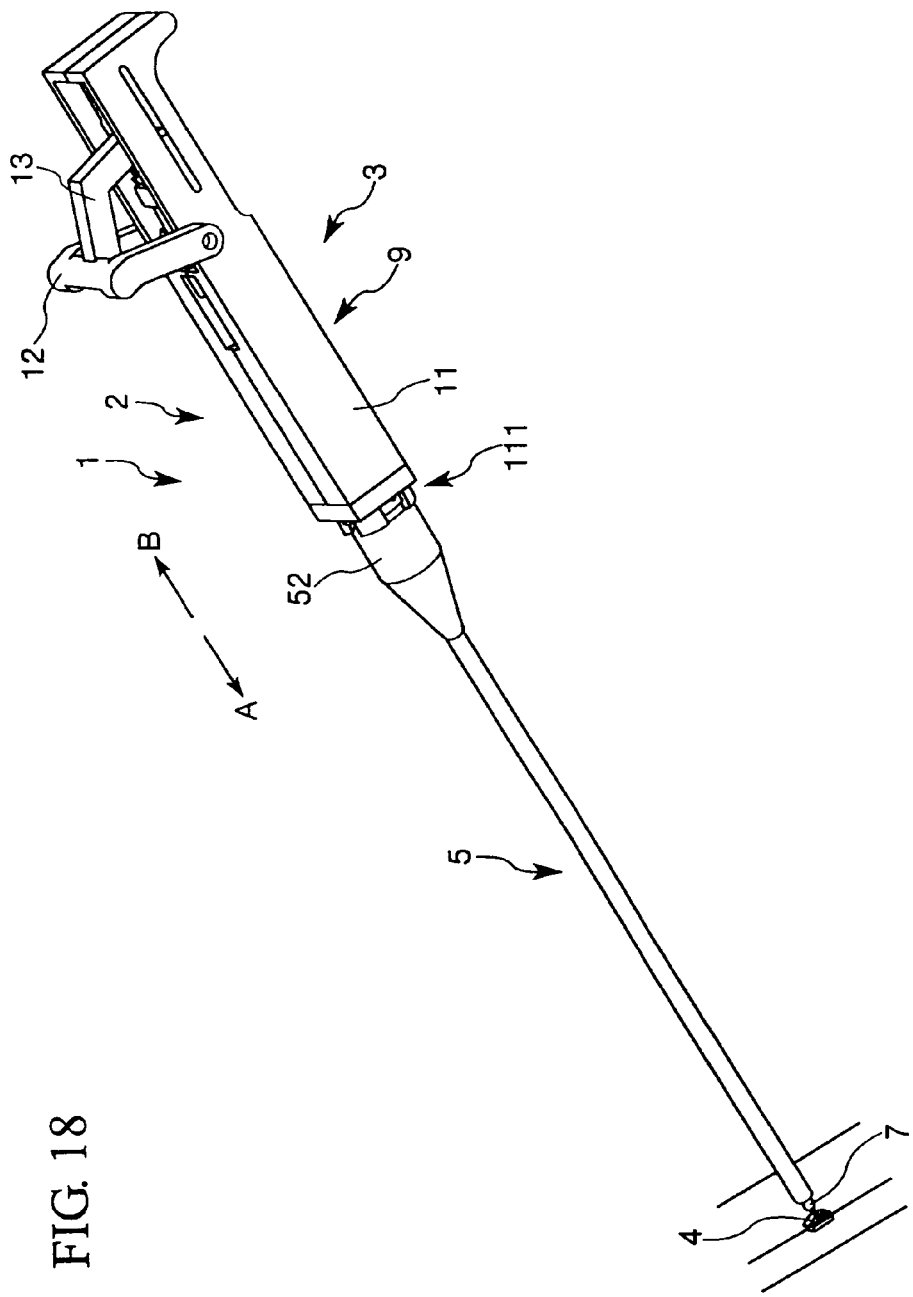

FIG. 18 is a perspective view of the distal end portion of the tissue closing device during operation.

Figure 19:
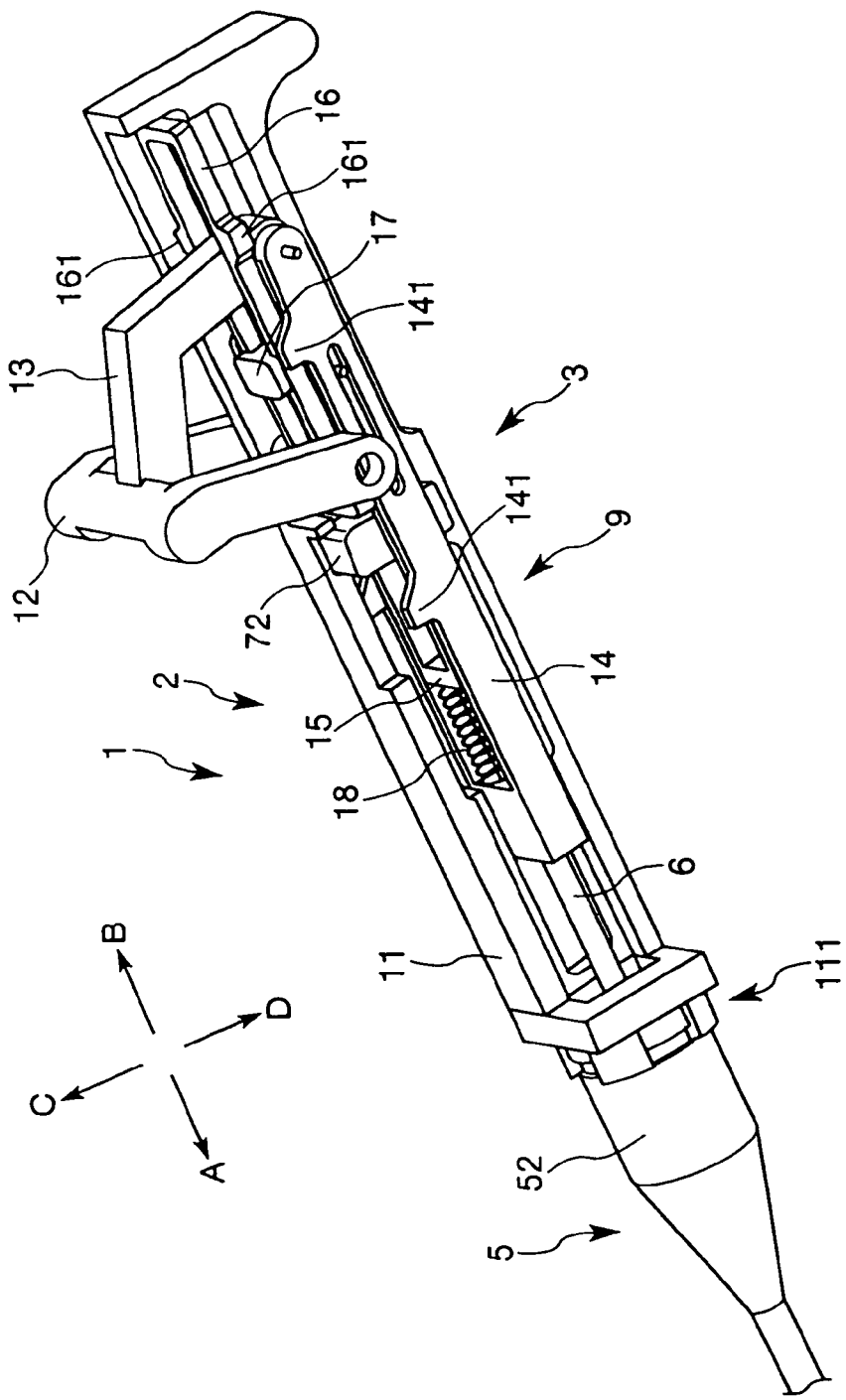

FIG. 19 is a perspective view of the tissue closing device during operation.

Figure 20:
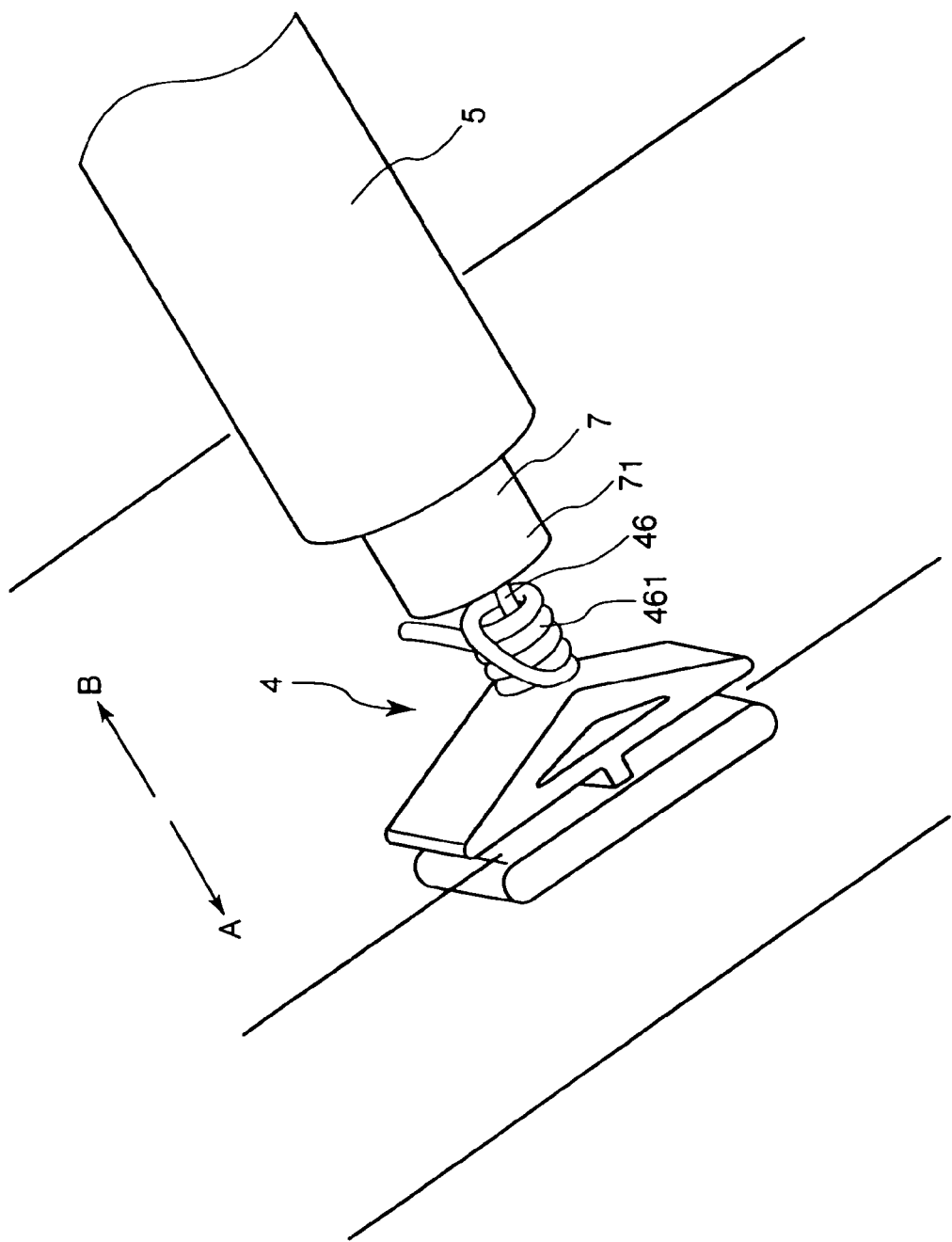

FIG. 20 is a perspective view of a portion of the tissue closing device during another operational aspect of the device.

Figure 21:
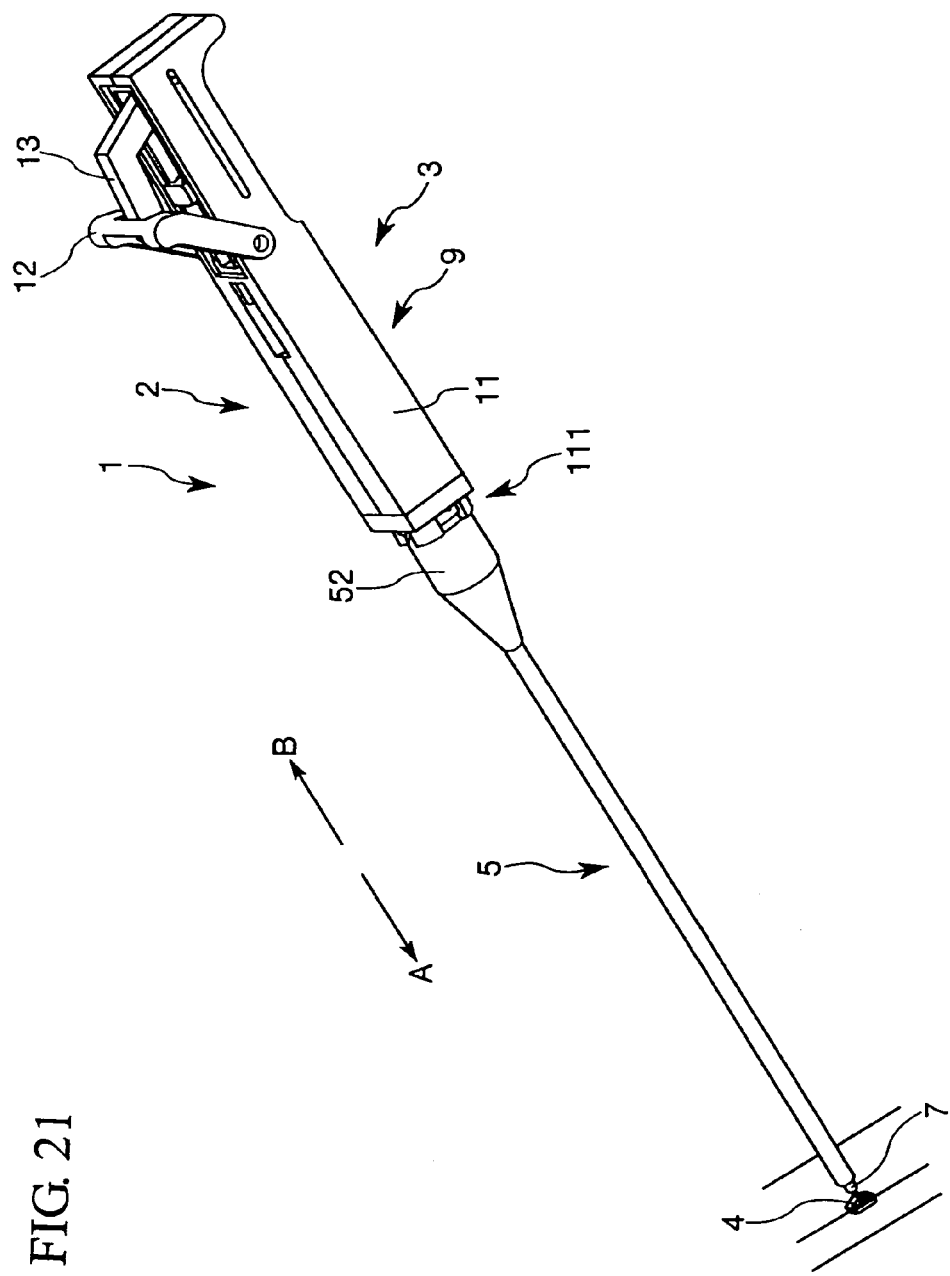

FIG. 21 is a perspective view of the tissue closing device during another operational aspect of the device.

Figure 22:
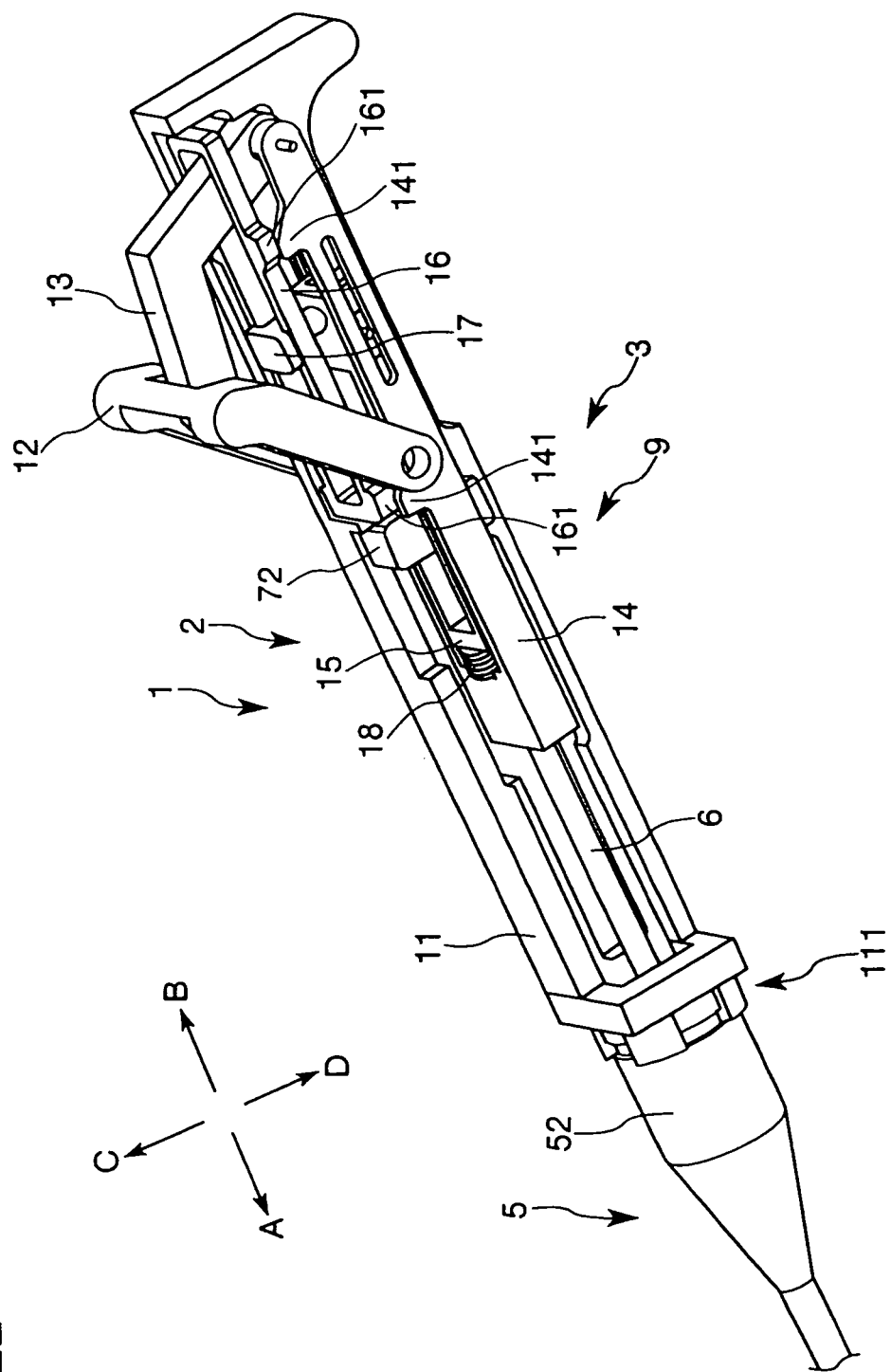

FIG. 22 is a perspective view of a portion of the tissue closing device during another operational aspect of the device.

Figure 23:
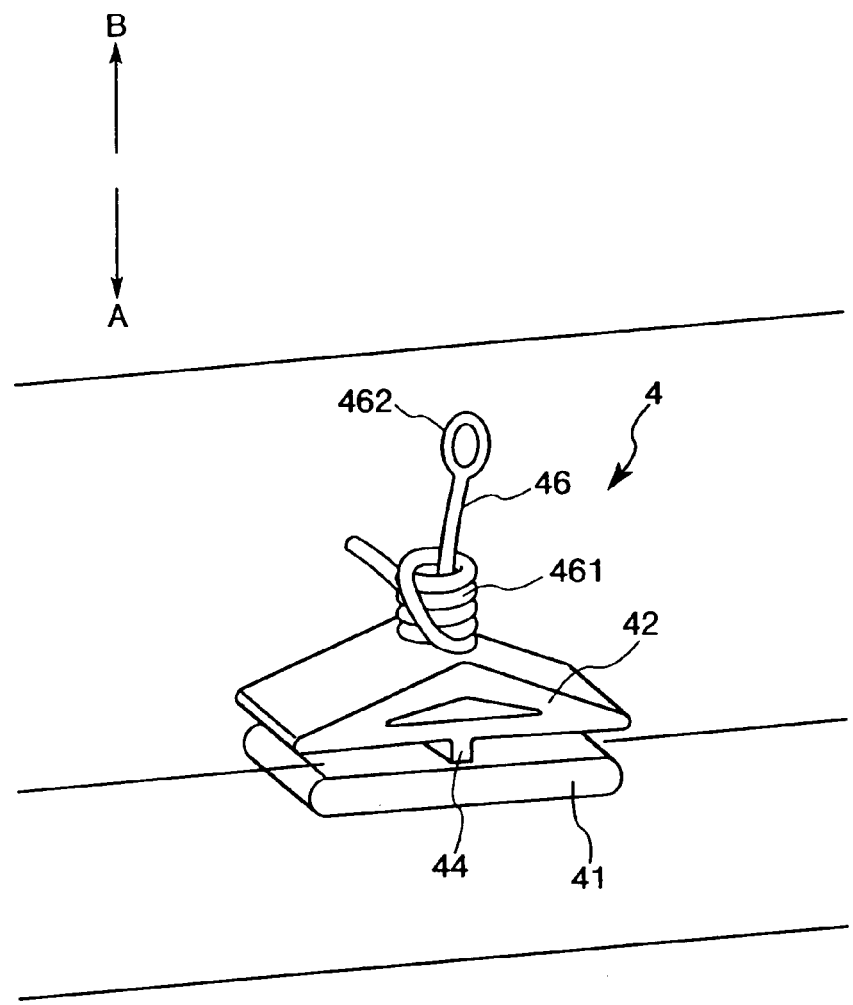

FIG. 23 is a perspective view of the clip in position closing an opening in a wall of a living body cavity.

DETAILED DESCRIPTION

For convenience in the description that follows, in FIG. 1 (as well as FIGS. 5-10 and FIGS. 12 to 23), the direction indicated by arrow A is referred to as the "distal" direction, the direction indicated by arrow B (hand-operated side) is referred to as the "proximal" direction, the direction indicated by arrow C is referred to as the "upper" direction, and the direction indicated by arrow D is referred to as the "lower" direction. Also, in FIGS. 2-4, and in FIG. 11, the upper side is referred to as "proximal", while the lower side is referred to as "distal".

The tissue closing device 1 generally shown in FIG. 1 is a device for closing or closing up a percutaneous penetrating opening (i.e., an opening penetrating a tissue membrane or living tissue). The opening penetrating the living tissue may be an opening formed in a wall of living body cavity such as a blood vessel, an internal organ of a living body, an internal tissue of a living body, etc.

Figure 2:
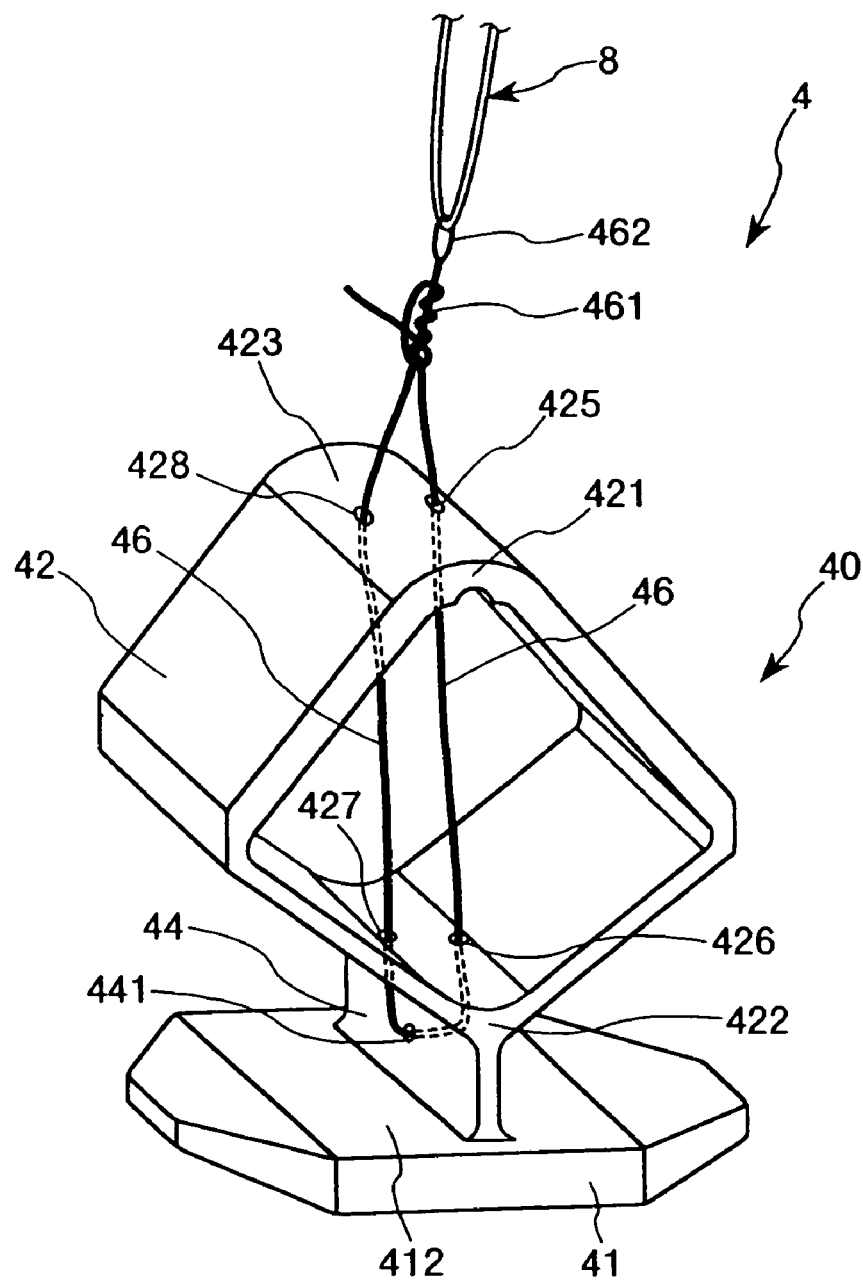
FIG. 2 is a perspective view of a clip used in the tissue closing device shown in FIG. 1.

As shown in FIGS. 1 and 2, the tissue closing device 1 includes an elongate arrangement device (feeding and deformation means) 3 which has a distal end portion adapted to pass through an opening penetrating living tissue (opening on a wall of living body cavity). The elongate arrangement device 3 includes an operational portion 9 on the proximal side, and a clip 4 serving as a closure (tissue closure) which is detachably retained at or connected to the distal end portion of the arrangement device 3 and which is adapted to close the opening penetrating the living tissue. In the illustrated and disclosed embodiment, the operational portion 9 is a hand-operated portion.

As shown in FIG. 2, the clip or closure 4 is comprised of a clip body (closure body) 40, and a thread (first thread-like member) 46 serving as a fixing portion. The clip body 40 is composed of a seal portion 41, a deformable deformation portion 42, and a connecting portion 44 connecting the seal portion 41 with the deformation portion 42. In addition, the thread 46 has a knot 461 and a ring 462. Additional details associated with the clip 4 will be described below.

The arrangement device 3 is adapted to be inserted in a sheath (elongate tube element) 5, generally shown in FIGS. 12-14. The sheath includes a distal end portion passing through (penetrating) an opening that penetrates living tissue and a central portion provided with a through-hole 51 extending in the axial direction. That is, the sheath includes a lumen open at opposite ends. The sheath 5 and the arrangement device 3 constitute an elongate body portion 2, although the sheath 5 may be considered a part separate from the elongate body portion 2. At the time of performing a staunching operation to close the opening penetrating the living tissue, the distal end portions of the sheath 5 and the arrangement device 3, together with the clip 4, penetrate the opening. In other words, the distal end portions of the sheath 5 and the arrangement device 3, and the clip 4, are inserted into a lumen of a living body (living tissue) such as a blood vessel via the opening.

The sheath 5 possesses a generally hollow cylindrical shape, and includes a hub 52 at its proximal end portion. In addition, a staunching valve (not specifically illustrated) is disposed on the inner circumferential side of the hub 52.

The sheath 5 can be, for example, similar to a sheath (introducer sheath) left indwelling after the procedure of therapy (PCI) or diagnosis (CAG) using a catheter or may be a sheath for exclusive use in the tissue closing device 1.

Figure 5:
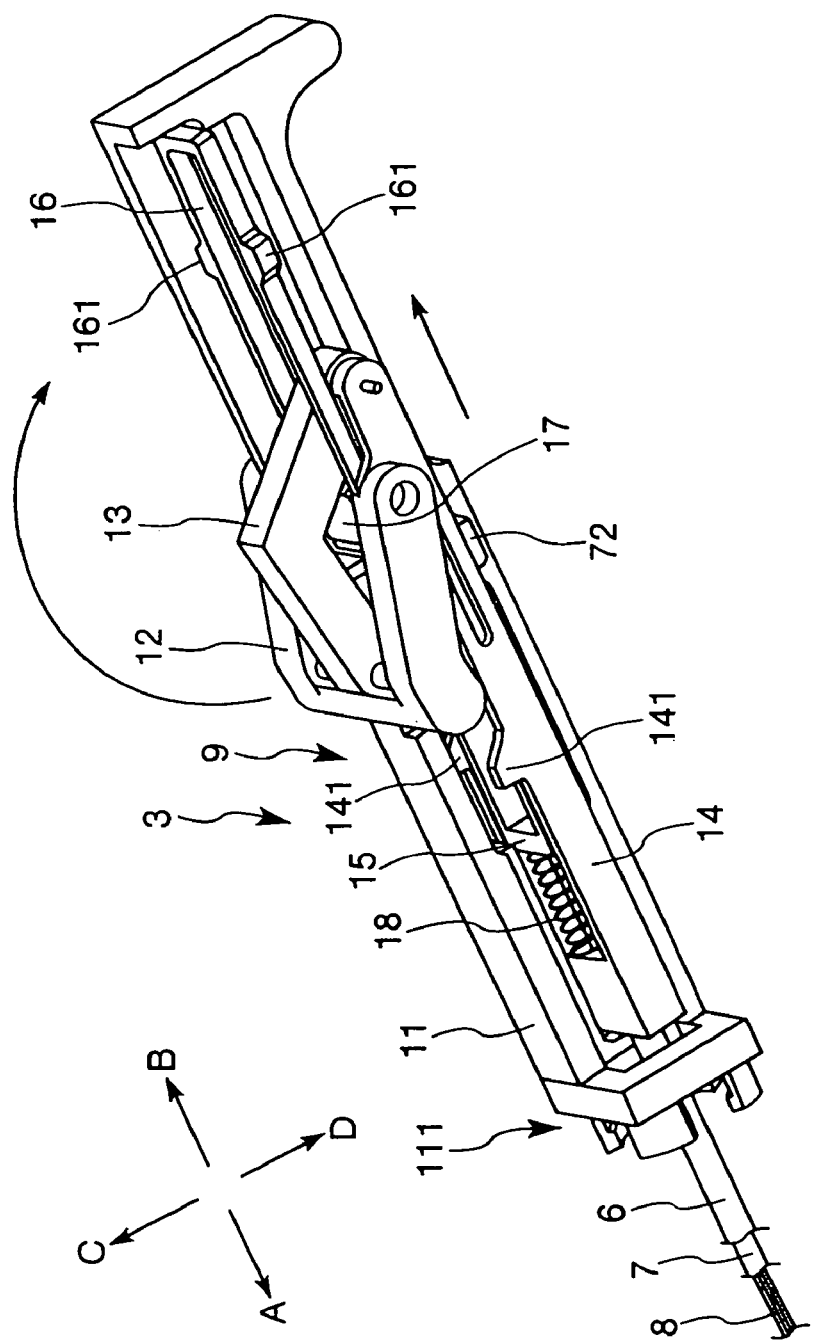
FIG. 5 is a perspective view of the inside structure of the hand-operated portion of the tissue closing device shown in FIG. 1.

As shown in FIGS. 2 and 5, the arrangement device 3 includes a thread (second thread-like member) 8 which serves as a retaining member (retaining means) detachably connected to the clip 4 (i.e., the thread 46 of the clip 4) to retain the clip 4; a cover member 6, serving as a cover means, in the form of an elongate first tubular member (tubular member) having a distal end portion capable of penetrating or extending through an opening penetrating living tissue (an opening on a wall of a living body cavity such as a blood vessel); a fixed tube 7, serving as a lock means, in the form of an elongate second tubular member (tubular member) positioned inside the cover tube 6 and having a distal end portion capable of penetrating or extending through the opening penetrating the living tissue; and a hand-operated portion 9. The clip 4 (the thread 46 of the clip 4) is detachably retained at a distal end portion of the arrangement device 3 by the thread 8.

The fixed tube 7 is disposed or inserted concentrically inside the lumen of the cover tube 6, with the cover tube 6 being movable relative to the fixed tube 7 in the axial direction by sliding movement. The thread 8 is disposed or inserted inside the lumen of the fixed tube 7 so as to be movable relative to the fixed tube 7 in the longitudinal direction of the fixed tube 7. The hand-operated portion 9 is positioned at the proximal side of the fixed tube 7 and the cover tube 6.

Figure 9:
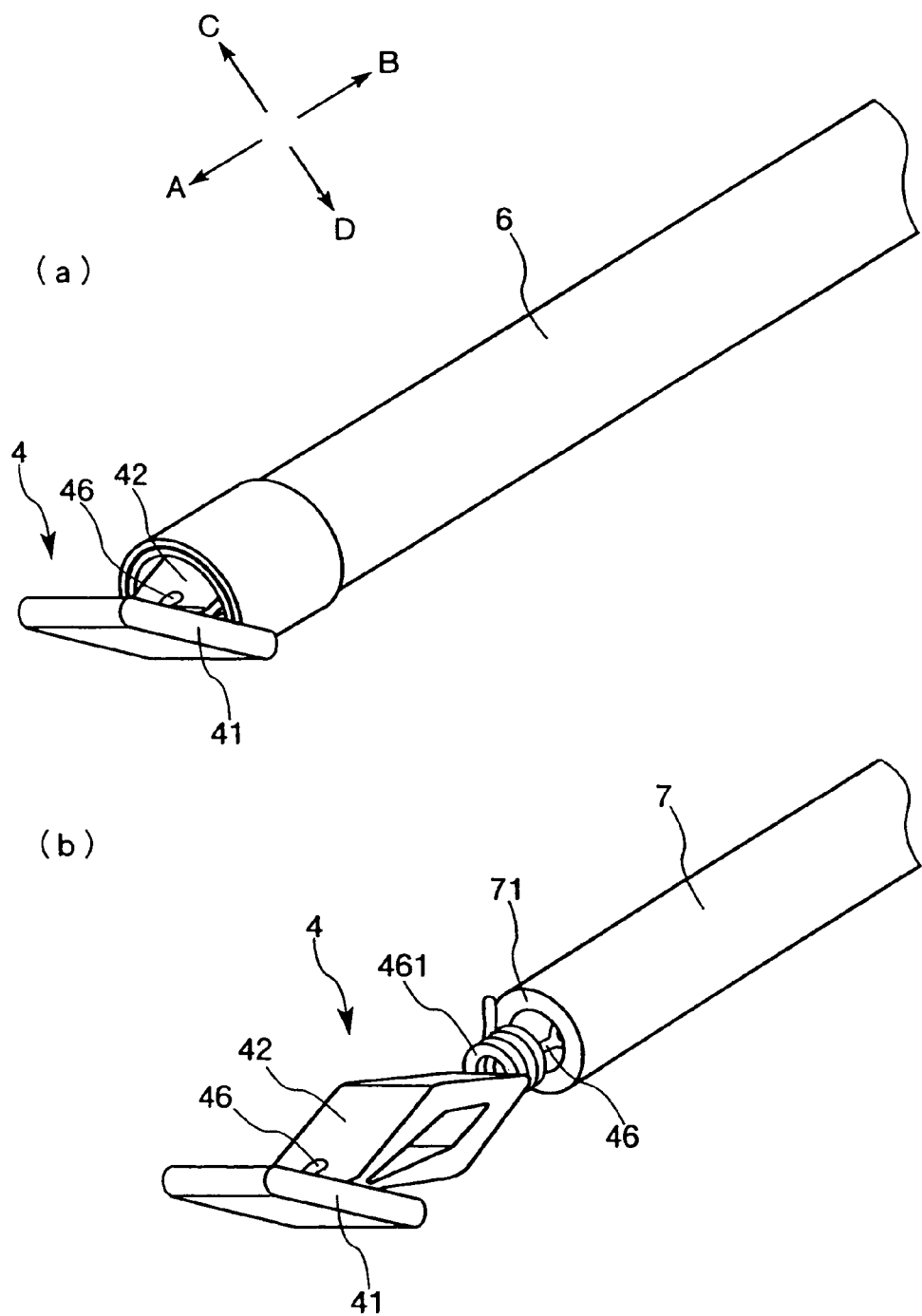
FIG. 9(a) is a perspective view of the distal end portion of the tissue closing device shown in FIG. 1 illustrating the cover tube and a portion of the clip positioned outside the cover tube.
FIG. 9(b) is a perspective view of the distal end portion of the tissue closing device shown in FIG. 1 illustrating the fixed tube and the clip.

The proximal end portion of the cover tube 6 is fixed to or supported on the distal end portion of a cover tube support portion 14 (see FIG. 5) of the hand-operated portion 9. This cover tube support portion 14 serves as a cover means support portion. As shown in FIG. 9, the deformation portion 42 of the clip 4 is detachably mounted or inserted in the distal end portion of the cover tube 6. In this case, the deformation portion 42 of the clip 4 is inserted and retained in the lumen of the distal end portion of the cover tube 6, whereby the clip 4 is mounted in place.

In addition, when the arrangement device 3 (cover tube 6) is inserted into the through-hole 51 of the sheath 5 from the proximal side of the sheath 5, the distal end portion of the cover tube 6 is exposed from the distal end of the sheath 5. That is, the distal end of the sheath 5 is located on the proximal side relative to the distal end of the cover tube 6.

With the cover tube 6 covering the outer surface of the fixed tube 7, and at a distal end portion thereof, also covering at least a part of the clip 4, the deformation portion 42 of the clip 4 in this embodiment is covered.

Figure 8:
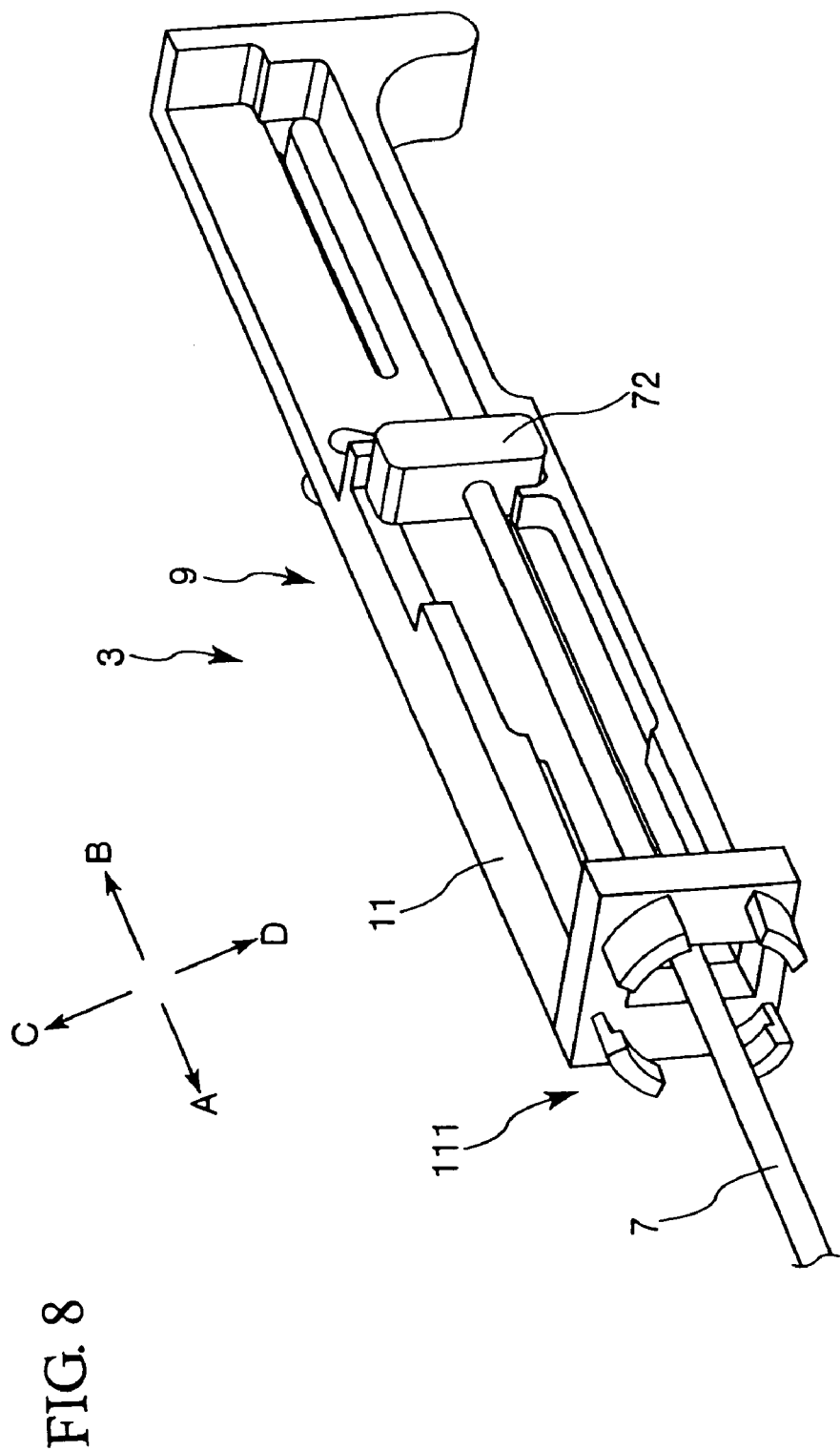
FIG. 8 is a perspective view of parts of the hand-operated portion of the tissue closing device shown in FIG. 1.

The fixed tube 7 is formed of a comparatively hard material and has a hub 72 at its proximal end portion as shown in FIG. 8. The hub 72 is located in the inside of a thread support portion 15 (identified in FIG. 5) of the hand-operated portion 9, and is fixed to or supported on the body 11 of the hand-operated portion.

In addition, when the fixed tube 7 of the arrangement device 3 is inserted into the through-hole 51 of the sheath 5 from the proximal side of the sheath 5 and positioned in the sheath 5, the distal end of the sheath 5 is located on the proximal side relative to the distal end of the fixed tube 7. In addition, as generally shown in FIG. 9(a), the distal end of the fixed tube 7 is located on the proximal side relative to the distal end of the cover tube 6.

The fixed tube 7 functions such that when the thread 46 of the clip 4 is pulled in the proximal direction by the thread 8, a knot 461 of the thread 46 of the clip 4 is locked to, or fixed in position relative to, the distal end portion 71 of the fixed tube 7. In addition, the deformation portion 42 is locked (indirectly locked) through the knot 461, whereby the knot 461 is moved relatively in the distal direction to tighten the thread 46 and deform the deformation portion 42.

As shown in FIGS. 1 and 5-8, the operational portion or hand-operated portion 9 includes: the operational portion body 11 (hand-operated portion body); an operating lever or operating portion 12; a stroke bar 13; the cover tube support portion 14 for supporting the cover tube 6; the thread support portion 15 for supporting the thread 8 so that the thread is operatively connected to the operating lever 12; a pin 17 (connection means) which is inserted in the thread support portion 15 and serves as a thread holder detachably connecting the thread 8 to the thread support portion 15 in a way that operatively connects the thread and the operating lever 12; a lifter 16 serving as a release member which releases the thread from the thread support portion 15 to operatively disconnect the operating lever 12 and the thread 8; and a coil spring 18.

The hand-operated portion body 11 has a box-like shape possessing a generally rectangular parallelepiped outside shape. A connector 111, which is adapted to be fitted in the hub 52 of the sheath 5, is provided at the distal end portion of the hand-operated portion body 11. The connector 111 includes four pawls or hook members which are adapted to engage the hub 52 of the sheath. In addition, the hand-operated portion body 111 is provided at its proximal end portion with a generally downwardly projecting projected portion functioning as a finger hook portion useful at the time of operation.

The cover tube support portion 14 and the thread support portion 15 are positioned in the inside of the hand-operated portion body 11 and are adapted to be individually movable in the longitudinal direction of the arrangement device 3.

In addition, the thread support portion 15 is disposed inside the cover tube support portion 14. The coil spring 18 is an elastic member capable of contracting and expanding along the moving directions of the cover tube support portion 14 and the thread support portion 15 and applied a biasing force. In the illustrated embodiment, the spring 18 is disposed between the distal end portion of the cover tube support portion 14 and the distal end portion of the thread support portion 15.

The lever 12 is positioned so as to be turnable or rotatable relative to the hand-operated portion body 11. In the illustrated embodiment, one end portion (i.e., the right end portion as shown in FIGS. 1 and 5) of the lever 12 is rotatably or turnably mounted on the hand-operated portion body 11. In addition, the proximal end portion of the stroke bar 13 is turnably or rotatably disposed at the proximal end portion of the cover tube support portion 14, and the distal end portion of the stroke bar 13 is turnably or rotatably disposed on the other end side of the lever 12 (i.e., the left end side in FIGS. 1 and 5). With this construction, when the lever 12 is operated (turned or rotated), the cover tube support portion 14 is moved by way of the stroke bar 13. As illustrated, the stroke bar 13 includes two portions angled relative to another so that the stroke bar 13 is generally L-shaped or V-shaped.

In this case, when the lever 12 is operated towards the proximal end side of the hand-operated portion 9 (i.e., is turned clockwise in FIGS. 1 and 5), the cover tube support portion 14 is moved in the proximal direction, whereas when the lever 12 is operated towards the distal end side of the hand-operated portion 9 (i.e., is turned counterclockwise in FIGS. 1 and 5), the cover tube support portion 14 is moved in the distal direction. When the assembly of the tissue closing device 1 is completed, the lever 12 is located in the manner shown in FIGS. 1 and 5, and the lever 12 is turned clockwise at the time of closing an opening penetrating living tissue.

As generally mentioned above, the stroke bar 13 is configured to include a central portion that is bent. This bent central portion projects away from the hand-operated portion body 11 in the illustrated condition of the lever 12 shown in FIGS. 1 and 5 in which the lever 12 is at rest in an initial condition closer to the distal end side of the hand-operated portion 9. Thus, in the initial condition of the lever 12, the point of connection between the stroke bar 13 and the lever 12 can be located on or below an extension or continuation of the straight line connecting the point of connection of the stroke bar 13 and the cover tube support portion 14 and a fulcrum point (turning axis) of the lever 12. Therefore, even when a force in the moving direction of the cover tube support portion 14 is exerted, the force is not exerted in the direction for moving the lever 12, so that the lever 12 and the stroke bar 13 can be prevented from being unwillingly moved (slipping off toward the proximal side) when the lever 12 is not operated.

Figure 10:
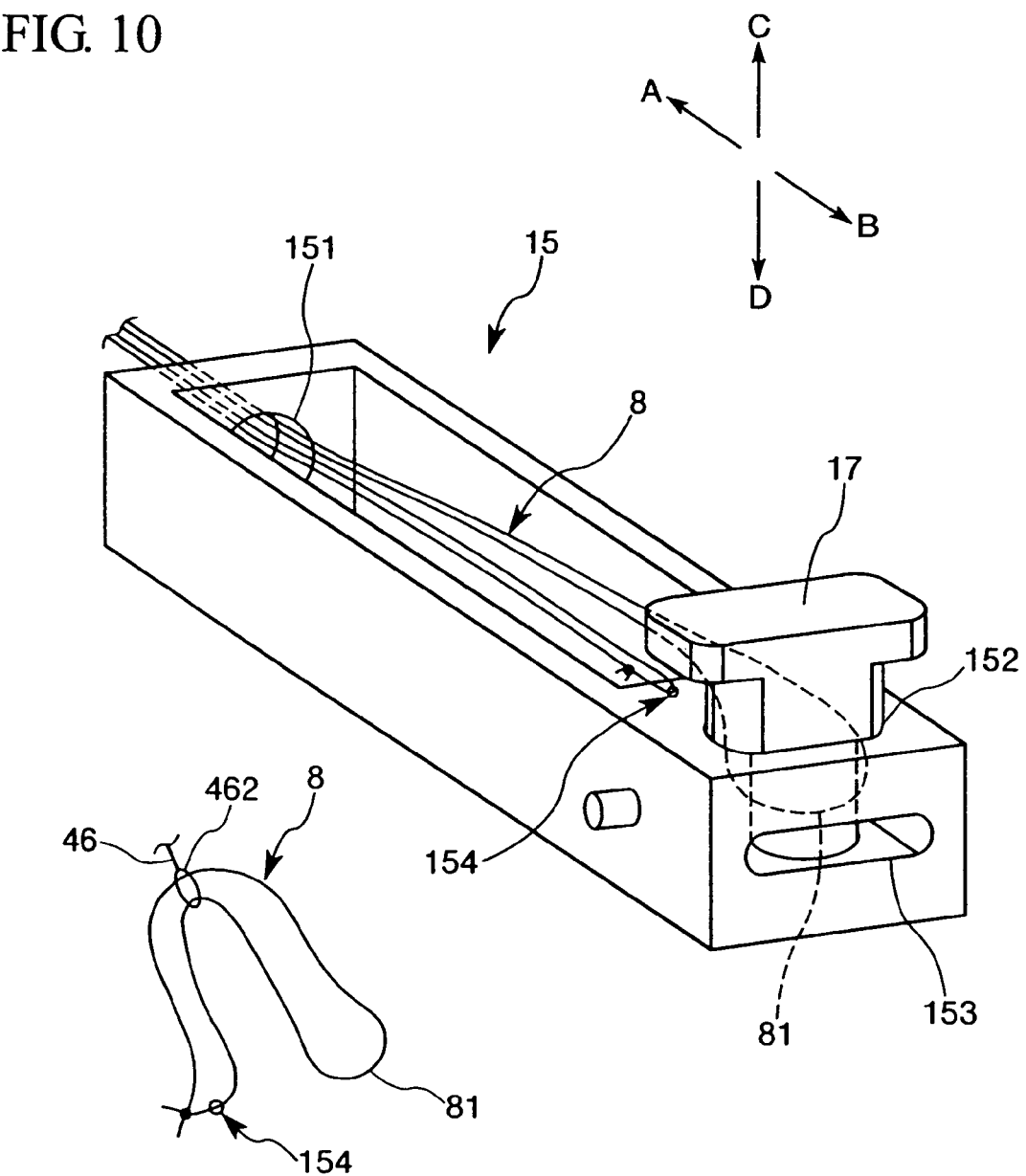
FIG. 10 is a perspective view of the thread support portion, pin and thread used in the tissue closing device shown in FIG. 1.

As shown in FIG. 10, the thread support portion 15 is provided at its distal end portion with a through hole or opening 151. The fixed tube 7 is adapted to pass through this opening 151. In addition, the proximal end portion of the thread support portion 15 is provided with a hole or opening 152 in which the pin 17 is inserted and a hole or opening 153 which is located correspondingly to the hole portion 152 and through which the thread 8 can be passed.

The thread 8 is composed of a double thread (double thread-like member) in which a single thread or thread-like member is bent back upon itself so that the bent-back portion 81 constitutes one end portion of the thread 8. In addition, the thread 8 is attached to the thread support portion 15 by a method in which the thread 8 in the form of a single thread is passed through a through hole or opening 154 formed in the proximal end portion of the thread support portion 15, with both end portions of the thread then being tied to each other.

The thread 8 is connected to the clip 4 by passing the thread 8 through the ring 462 of the thread 46 of the clip 4 and is bent back at a distal end portion of the arrangement device 3. In the condition where the thread 8 retains the clip 4, the pin 17 is passed through the loop of the bent-back portion 81, and the bent-back portion 81 is detachably connected to the thread support portion 15 by the pin 17. As described above, the other end portion (the end portion on the opposite side of the bent-back portion 81) is attached to the thread support portion 15.

At the time of passing the pin 17 through the loop of the bent-back portion 81 of the thread 8, the bent-back portion 81 is drawn out from, or pulled through, the through hole 153 to the exterior, and the pin 17 is inserted into the hole portion 152.

Figure 6:
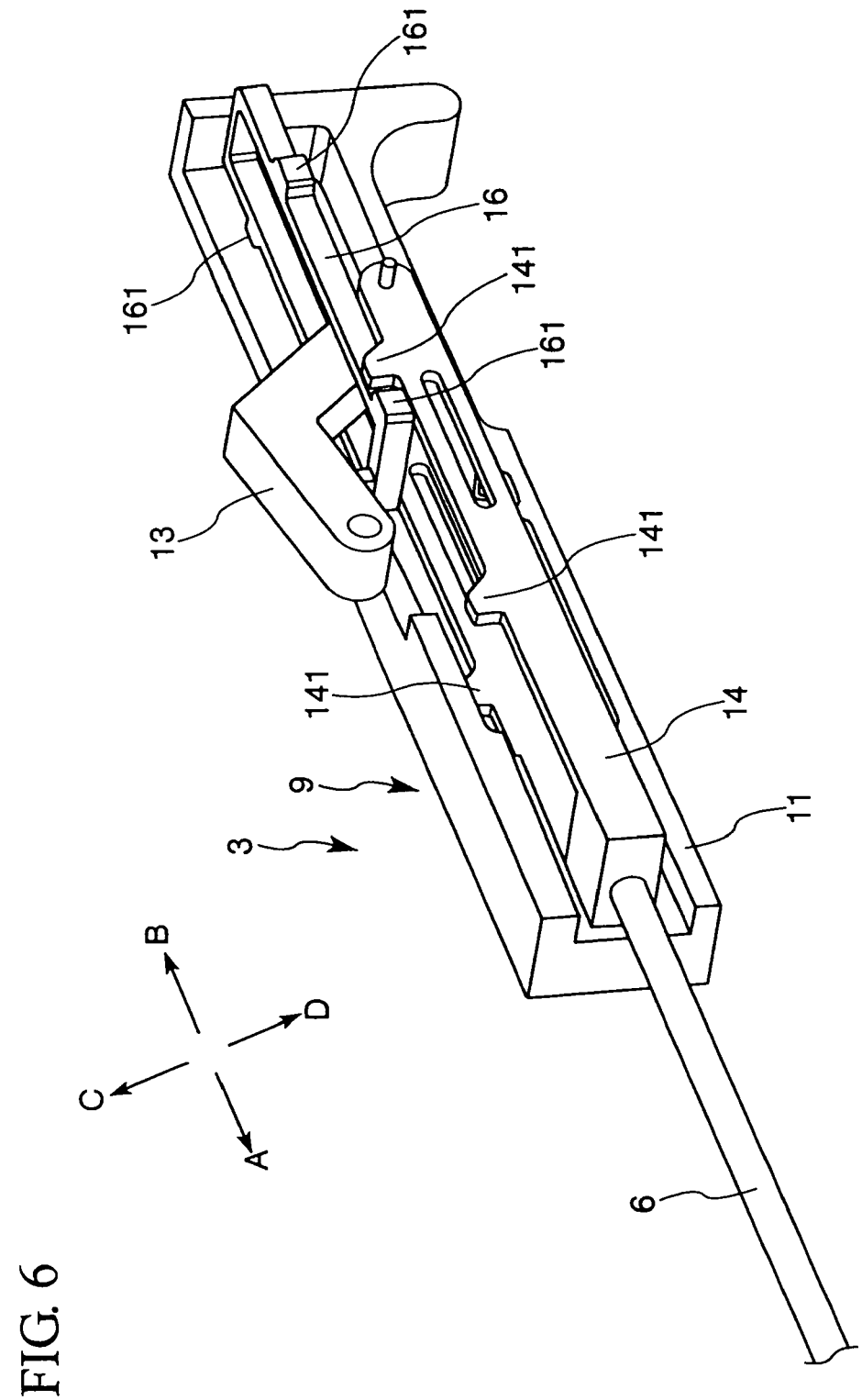
FIG. 6 is a perspective of parts of the hand-operated portion of the tissue closing device shown in FIG. 1.
Figure 7:
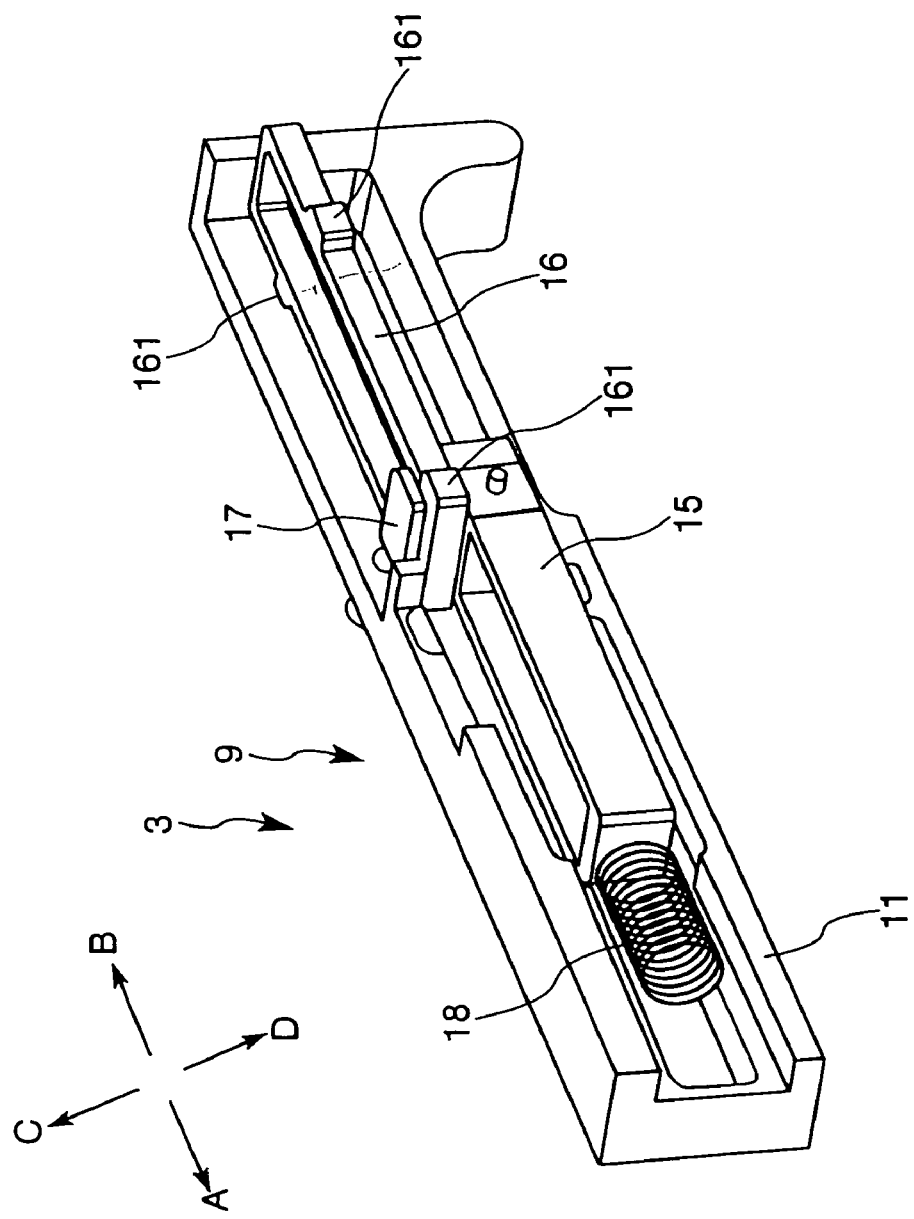
FIG. 7 is a perspective view of parts of the hand-operated portion of the tissue closing device shown in FIG. 1.

As shown in FIGS. 5-7, in the inside of the hand-operated portion body 11, a lifter 16 is disposed in an upwardly movable or displaceable manner. The lifter 16 is positioned on the proximal end side of the cover tube support portion 14. The lifter 16 has a frame-like shape and is disposed so that the hole 152 in which the pin 17 is inserted is located in the inside of the frame, in plan view. This ensures that when the pin 17 is inserted in the hole 152, the pin 17 is supported by or overlies the lifter 16.

In addition, the lifter 16 is provided with four projections (first projections) 161. Each of the first projections 161 projects sideways or laterally from a side portion of the lifter 16.

The cover tube support portion 14 is provided with four projections (second projections) 141 which serve as displacement portions that move or displace the lifter 16 upwardly when the projections 141 abut the corresponding projections 161 of the lifter 16. Each of the projections 141 projects upward from an upper portion of the cover tube support portion 14 as illustrated in FIG. 6. As also illustrated in FIG. 6, the proximally facing end surfaces of the projections 141 are inclined relative to the vertical.

When the cover tube support portion 14 is moved in the proximal direction by operating the hand-operated portion 9, namely, by a turning operation of the lever 12, the thread support portion 15 is moved in the proximal portion by way of the cover tube support portion 14. More specifically, as described above, the spring 18 disposed between the distal end portion of the cover tube support portion 14 and the distal end portion of the thread support portion 15 applies a bias force between the cover tube support portion 14 and the thread support portion 15 so that when the cover tube support portion 14 is moved in the proximal direction, the thread support portion 15 is pushed by the cover tube support portion 14 through the spring 18 so that the thread support portion 15 initially also moves in the proximal direction. When the deformation of the deformation portion 42 of the clip 4 is completed and the movement of the thread support portion 15 is stopped, only the cover tube support portion 14 can be moved further in the proximal direction by contraction of the spring 18.

Then, when the cover tube support portion 14 is moved further in the proximal direction by operating the hand-operated portion 9, the projections 161 of the lifter 16 are pushed upward by the projections 141 to move the lifter 16 upwards. The upward movement of the lifter 16 causes the overlying pin 17 to be moved upwardly in the direction allowing the pin 17 to come off of the thread support portion 15. The connection between the thread 8 and the thread support portion 15 by the pin 17 is canceled (i.e., the thread 8 and the thread support portion 15 become uncoupled), whereby the connection between the thread 8 and the clip 4 is canceled (i.e., the thread 8 and the clip become uncoupled). That is, the retained state of the clip 4 by the thread 8 is canceled. Therefore, the projections 161 and the projections 141 constitute a canceling means for canceling the connection between the thread 8 and the clip 4 (or the connection between the thread 8 and the lever 12 of the arrangement device 3), namely, for canceling the retained state of the clip 4 by the thread 8.

Features associated with the clip or closure 4 will now be described with reference to FIG. 2. The clip 4 includes a clip body (closure body) 40 and the thread (first thread-like member) 46 serving as a fixing portion. The clip body 40 is composed of the seal portion 41, the deformable deformation portion 42, and the connecting portion 44 connecting the seal portion 41 and the deformation portion 42 to each other. Preferably, the seal portion 41, the deformation portion 42 and the connecting portion 44 (i.e., the entirety of the clip body 40) are integrally formed in one piece of the same material.

The seal portion 41 is a member possessing a generally plate-shaped configuration having a flat surface portion (flat surface) 412 for covering an opening penetrating a living tissue and a peripheral portion of the opening by making close contact with the peripheral portion of the opening in the living tissue from one side (i.e., the inner surface) of the wall of living tissue.

The surface of the seal portion 41 to which the deformation portion 42 is connected (i.e., the surface on the upper side in FIG. 2) is a substantially flat surface.

The deformation portion 42 has a pantograph-like shape composed of a roughly rhombic frame-like body, and is linked or connected through the connecting portion 44 to a substantially central area of the flat surface portion 412 of the seal portion 41.

More specifically, the deformation portion 42 has a frame-like shape capable of being deformed between a first form in which the deformation portion 42 is expanded in a direction substantially perpendicular to the seal portion 41 and contracted in a direction substantially parallel to the seal portion 41, and a second form in which the deformation portion 42 is contracted in a direction substantially perpendicular to the seal portion 41 and expanded in a direction substantially parallel to the seal portion 41. Therefore, the deformation portion 42 can be deformed from a fundamental form or configuration (fundamental shape) shown in FIG. 2 to an arbitrary form or configuration between the first form and the second form, for example a form allowing the clip 4 to pass through an opening penetrating living tissue, and a form enabling closure of the opening by clamping the wall of the living tissue between the deformation portion 42 and the seal portion 41 from the other face (outer face) side.

In the case where the wall of the living tissue (living body cavity) is a blood vessel wall, the one face is the inner face of the blood vessel wall at the inner side of the blood vessel, and the other face is the outer face of the blood vessel wall at the outer side of the blood vessel.

In this illustrated and described embodiment, the deformation portion 42 is a portion having a polygonal annular shape formed by bending a belt-like member a plurality of times (a quadrangular annular shape formed by bending a belt-like member four times). More specifically, the deformation portion 42 possesses a quadrangular shape (quadrangular frame-like shape) having four links joined integrally to each other and having four corner portions which function in a hinge-like manner allowing adjacent links to move relative to one another. Of the two corner portions 421, 422 positioned at diagonally opposite positions in the vertical direction in FIG. 2, the corner portion 422 on the lower side (the seal portion 41 side) in FIG. 2 is connected through the connecting portion 44 to a substantially central area of the flat surface portion 412 of the seal portion 41, and serves as an immovable portion which cannot move relative to the upper end of the connecting portion 44.

The configuration of the clip 4 described above allows the deformation portion 42 to be deformed so that the corner portion 421 and the corner portion 422 move closer to and farther away from each other from the arrangement shown in FIG. 2. That is, the deformation portion 42 of the clip 4 can be deformed in an expanding and contracting manner in two directions orthogonal to each other, and can rock or be tilted relative to the seal portion 41.

In addition, the corner portion 421 on the upper side in FIG. 2 (the side of the deformation portion opposite the seal portion 41) has an upper surface (the surface on the opposite side of the seal portion 41) 423 in the shape of a curved convex surface. The corner portion 421 of the deformation portion 42 is also provided near its center with two holes (through-holes) 425, 428, and the corner portion 422 is provided near its center with two holes (through-holes) 426, 427.

In addition, the connecting portion 44 has a plate-like shape and is provided with a hole (through-hole) 441 near the center thereof. By virtue of the connecting portion 44, the seal portion 41 and the corner portion 422 of the deformation portion 42 are spaced from each other by a predetermined distance.

Figure 3:
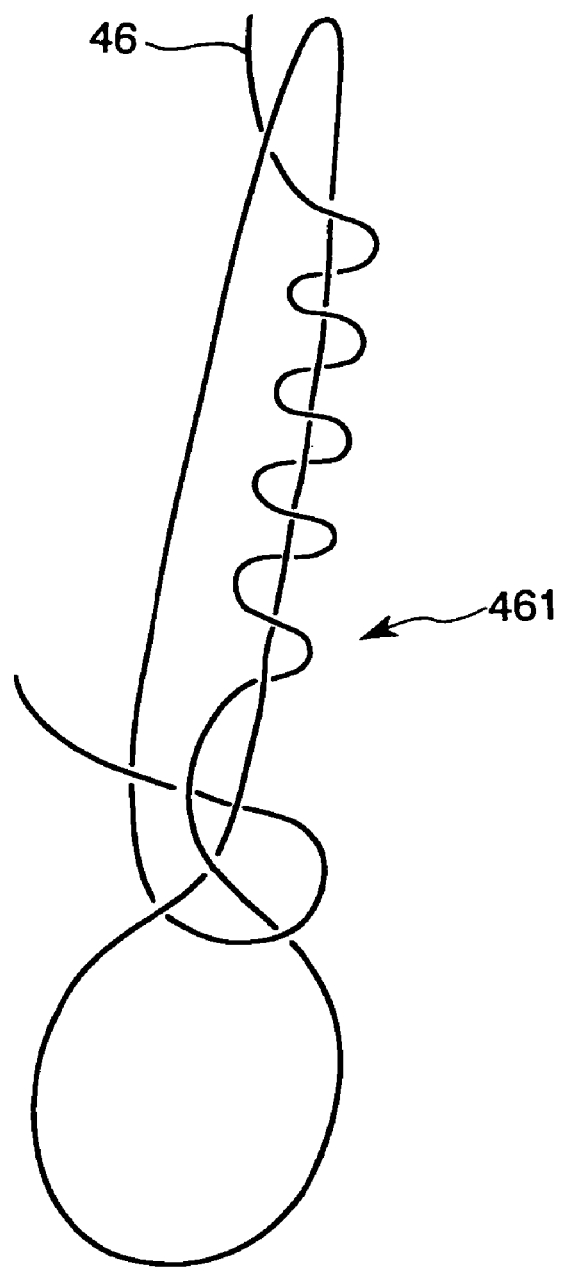
FIG. 3 illustrates an example of a knot used in connection with the tissue closing device shown in FIG. 1.
Figure 4:
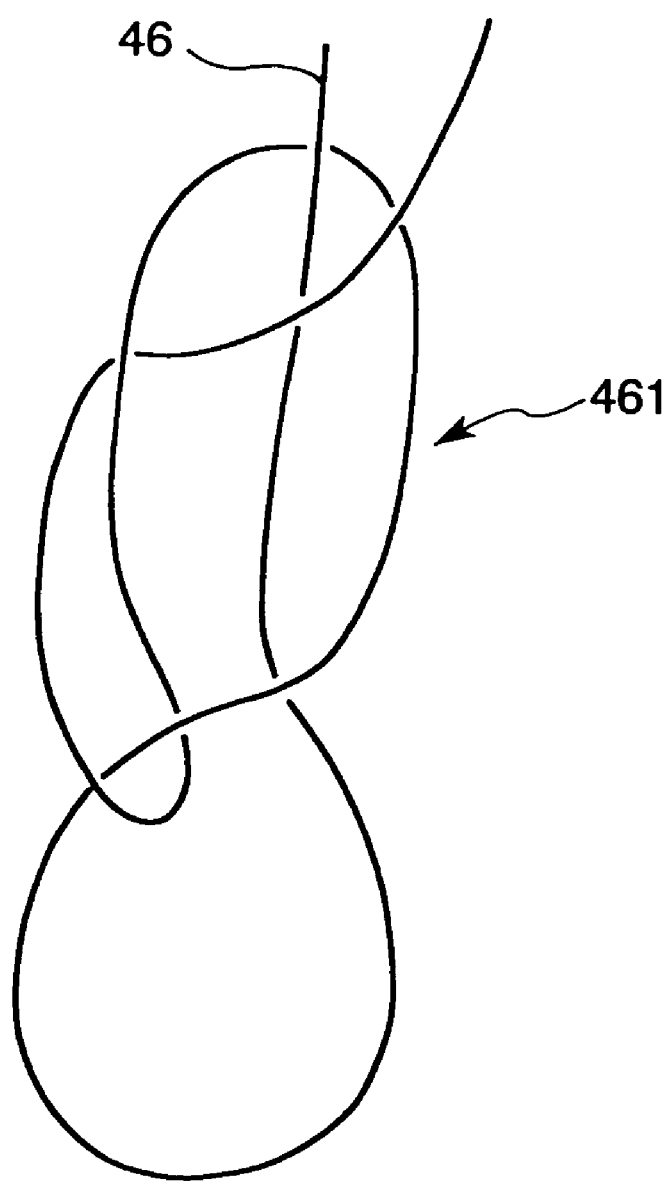
FIG. 4 illustrates another embodiment of a knot used in the tissue closing device shown in FIG. 1.

The thread 46 is hooked on an end portion side of the deformation portion 42, on the side opposite the seal portion 41, and on an end portion side of the deformation portion 42 on the side of the seal portion 41, and is attached to the clip body 40. In this embodiment, the thread 46 is hooked on the corner portion 421 of the deformation portion 42 (the end portion on the side of the deformation portion 42 opposite the seal portion 41) and the connecting portion 44 while penetrating the corner portion 421 of the deformation portion 42 and the connecting portion 44. Specifically, the thread 46 passes through or penetrates, sequentially from the upper side in FIG. 2, the hole 425 in the corner portion 421 of the deformation portion 42, the hole 426 in the corner portion 422, the hole 441 in the connecting portion 44, the hole 427 in the corner portion 422, and the hole 428 in the corner portion 421, with a knot 461 shaped as shown in FIGS. 3 and 4 being formed on the outside of the deformation portion 42 at a position adjacent the side of the corner portion 421. Such a knot is called clinch knot. In addition, a ring 462 through which to pass the thread 8 is formed on the upper side of the knot 461 as shown in FIG. 2.

The knot 461 is of such a nature that it is movable in the distal direction, namely downward in FIG. 2. With the knot 461 moved on the thread 46 in the distal direction so as to tighten the thread 46, the deformation portion 42 is deformed into a predetermined form between the first form and the second form, and this condition can be maintained. While the thread 46 maintains the condition where the deformation portion 42 is in the predetermined form, the knot 461 is located at an end portion on the opposite side of the seal portion 41, i.e., at the corner portion 421. Due to the strong tension on the thread 46, the knot 461 would not naturally move in the proximal direction unless a strong force is exerted.

The knot 461 is formed to have outer dimensions greater than the inside diameter of the fixed tube 7, and the ring 462 is formed to be smaller in outer dimensions than the inside diameter of the fixed tube 7. This ensures that at the time of moving the knot 461 of the thread 46 of the clip 4 by the fixed tube 7 and tightening the thread 46 to deform the deformation portion 42, the ring 462 can be led into the lumen of the fixed tube 7, whereas the knot 461 is prevented from entering into the lumen of the fixed tube 7. Therefore, the knot 461 can be moved in a reliable manner. In this way, the thread 46 functions as a fixing portion for the deformation portion 42 in that it fixes the deformation portion in the desired deformed configuration or form.

As has been described above, the thread 8 is passed through the lumen of the fixed tube 7 in the state of being passed through the ring 462 of the thread 46.

In the description above, the thread 46 and the thread 8 have been described as being separate threads or thread members. However, it is to be understood that the thread 46 and the thread 8 may be formed of the same thread (e.g., a single thread). Thus, the clip or closure 4 is connected to the tread support portion 15 by way of a connection element that can be in the form of two threads 46, 8 or a single thread.

In addition, the thread 46 may be composed of a double thread (double thread-like member) in which a single thread (thread-like member) is bent back, and the bent-back portion constitutes one end portion, and the ring 462 may be formed of the bent-back portion.

Preferably, at least a part of the clip body 40 of the clip 4 is formed of a bioabsorbable material. Particularly, a major part (majority part) of the clip body 40 is preferably formed wholly integrally of a bioabsorbable material. This allows the major part of the clip body 40 to be absorbed into a living body after a predetermined period of time, and will not be left or remain in the living body. Thus influences of the clip body 40 on the human body can be avoided. In addition, the thread 46 is preferably formed of a bioabsorbable material.

Examples of the bioabsorbable material which can be used include polylactic acid, polyglycolic acid, polydioxanone, etc., used singly, and complexes thereof.

The material constituting the clip body 40 of the clip 4 is not limited to the bioabsorbable material, and may be a biocompatible material such as a resin, a metal, etc. In addition, the material constituting the thread 46 is also not limited to bioabsorbable materials.

With respect to the physical properties required of the clip body 40 of the clip 4, it is preferable from the standpoint of the deformation function associated with the deformation portion 42 that the material possess excellent hinge characteristics. Specifically, a material having a tensile strength of 250 to 500 ($Kg/cm^2$), an elongation of 150 to 800%, a tensile modulus of 8 to 20 ($\times 103$ $Kg/cm^2$), and a bending strength of 300 to 700 ($Kg/cm^2$) is preferable. With these characteristics, the clip body 40 possesses excellent hinge characteristics and a desired degree of deformability of the deformation portion 42.

Figure 11:
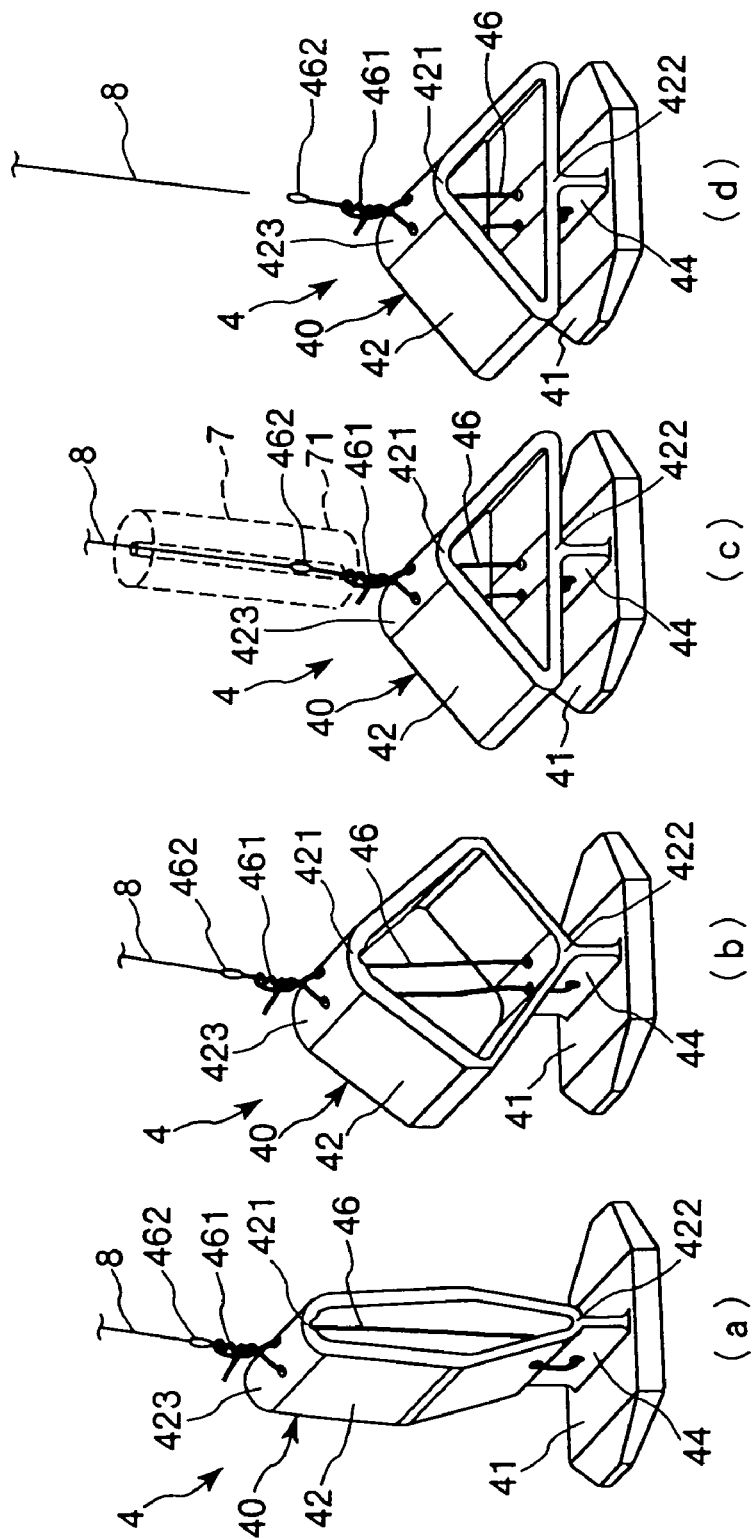

As shown in FIG. 11, when the thread 46 of the clip 4 is pulled in the proximal direction by the thread 8 in the condition where the deformation portion 42 of the clip 4 has come off a distal end portion of the cover tube 6 so that the deformation portion 42 can be deformed, the knot 461 of the thread 46 of the clip 4 is locked on the distal end portion 71 of the fixed tube 7, the deformation portion 42 is locked (indirectly locked) through the knot 461, whereby the knot 461 is moved in the distal direction, the thread 46 is tightened, and the deformation portion 42 is deformed.

In this case, where the clip 4 is mounted on the cover tube 6, the deformation portion 42 of the clip 4 is in a form in which it is expanded in a direction substantially perpendicular to the seal portion 41 and contracted in a direction substantially parallel to the seal portion 41 as shown in FIG. 11(a). As the knot 461 is moved in the distal direction and the thread 46 is tightened, the corner portion 421 of the deformation portion 42 is gradually moved downward in FIG. 11(a) toward the opposite corner 422, and the deformation portion 42 is continuously deformed from the form shown in FIG. 11(a) to the form shown in FIG. 11(b), and then to a form shown in FIG. 11(c) which allows the clip 4 to close an opening penetrating living tissue by clamping a tissue wall between the seal portion 41 and the deformation portion 42. That is, the deformation portion 42 is gradually contracted in the direction substantially perpendicular to the seal portion 41 and is gradually expanded in the direction substantially parallel to the seal portion 41.

In addition, as has been described above, the knot 461 is of such a nature that it can be moved in the distal direction only when a strong force is exerted thereon, and so the condition where the deformation portion 42 is in a predetermined form is maintained by the thread 46 (the knot 461).

Thus, the degree of deformation of the deformation portion 42 of the clip 4 can be continuously regulated (adjusted) so that the distance between the two corner portions 421, 422 can be continuously regulated (adjusted). That is, the condition where the deformation portion 42 assumes a desired form can be maintained. This makes it possible to use the clip 4 in a variety of situations such as a person whose living tissue wall, for example blood vessel wall, is thick, a person whose living body tissue wall is thin, a person whose living tissue wall is hard, a person whose living tissue wall is soft, etc. Thus, the clip has useful application to in various conditions (statuses) of the living body tissue.

As discussed above, the clip 4 possesses the seal portion and the deformation portion. The description above describes, and the drawing figures illustrate, one possibility for configuring and arranging the seal portion and the deformation portion. However, it is to be understood that the configuration of the clip (closure) is not limited in this regard as other configurations of the clip, including a seal portion and a deformation portion, are possible.

For example, the shape of the deformation portion of the clip is not limited to a quadrangle, but may be other polygonal or a corner-less frame-like shapes such as a circular annular shape, an elliptical annular shape, etc.

In addition, the deformation portion of the clip may be composed of a spongy porous member (porous material) or woven/non-woven fibrous aggregate plug containing, for example, a resin material (synthetic resin material) as a main material. The deformation portion can be a compressible plug made of, for example, bioabsorbable material such as collagen.

In addition, the fixing portion of the clip is not limited to the thread-like member.

A procedure for using or operating the tissue closing device 1 for performing a staunching operation to close an opening penetrating a wall of a living tissue will be described.

As shown in FIG. 12, after, for example, a treatment for therapy (PCI) or diagnosis (CAG) using a catheter, the sheath 5 is left indwelling in the living tissue (e.g., blood vessel) so that the sheath 5 can be used with the tissue closing device 1. A distal end portion of the sheath 5 passes through the opening that penetrates the living tissue (e.g., blood vessel) so that the distal end is located in the blood vessel.

Next, as shown in FIG. 13, an operator gradually inserts the arrangement device 3 into the through-hole 51 of the sheath 5 from the proximal side of the sheath 5, and fits the connector 111 of the arrangement device 3 and the hub 52 of the sheath 5 to one another. To insert the arrangement device 3 in the sheath 5, the seal portion 41 of the clip or closure 4 is preferably tilted or rocked relative to the connecting portion 44 and the deformation portion 42 so that the seal portion 41 is oriented generally in the manner shown in FIG. 9(a). This helps facilitate insertion of the distal end portion of the arrangement device 3 into the sheath 5. When the connector 111 of the arrangement device 3 and the hub 52 of the sheath 5 are connected to one another, the distal end portion of the cover tube 6 protrudes from the distal end portion of the sheath 5 as shown in FIGS. 14 and 15, and the seal portion 41 of the clip 4 protrudes from the distal end of the cover tube 6 so as to be inserted in the blood vessel.

Subsequently, as shown in FIGS. 16 and 17, the body portion 2 (the arrangement device 3) is slowly moved in the direction causing the body portion 2 to be pulled out of the opening penetrating the living tissue to cover the opening and the periphery of the opening with the seal portion 41 of the clip 4 from the inside of the living tissue (blood vessel) so that the seal portion 41 is positioned in facing and contact relation to the inside of the blood vessel. The deformation portion 42 of the clip 4 is moved to the outside of the blood vessel.

While performing the procedure of covering the opening and the periphery of the opening with the seal portion 41, when the operator senses resistance upon the seal portion 41 being adjacent the opening and the peripheral tissues (abutment resistance) during movement of the body portion 2 in the direction of pulling the body portion 2 out of the opening, the operator judges that the seal portion 41 has come into abutment on, or contact with, the opening and the peripheral tissues, thus determining that the positioning of the seal portion 41 has been completed.

Next, the lever 12 of the hand-operated portion 9 is turned. This causes the cover tube support portion 14 together with the cover tube 6 to move in the proximal direction relative to the deformation portion 42 of the clip 4. The deformation portion 42 thus comes off (i.e., moves out of) the distal end portion of the cover tube 6, resulting in the deformation portion 42 being capable of being deformed. As the lever 12 continues to be turned, the thread 46 of the clip 4 is pulled by the thread 8, the deformation portion 42 is locked on or bears against the distal end portion 71 of the fixed tube 7, and the deformation portion 42 is deformed (i.e., the deformation portion is deformed towards the form shown in FIG. 11(*d*)). This operation thus causes the clip or closure 4 to be subjected to oppositely directed forces (a force in the proximal direction produced by the pulling of the thread 8 and a force in the opposite or distal direction produced by the fixed tube 7 or the knot 461) which cause the deformation portion 42 to be deformed. After the deformation of the deformation portion 42 is completed, the force applied by the thread 8 to the clip 4 (the retained state of the clip 4 by the thread 8) is canceled or released. This series of operations is performed continuously in one operational movement of the lever 12 in a single direction. These operations will be sequentially described below in more detail.

As generally shown in FIGS. 18-20, as the lever 12 of the hand-operated portion 9 is turned, the cover tube 6 is first moved in the proximal direction relative to the deformation portion 42 of the clip 4, together with the cover tube support portion 14. The deformation portion 42 thus comes off or becomes separated from the distal end portion of the cover tube 6, resulting in the deformation portion 42 being deformable.

In addition, as the cover tube support portion 14 moves in the proximal direction, the thread support portion 15 is pushed by the cover tube support portion 14 through the spring 18 and also moves in the proximal direction. The thread 8 is thus also moved in the proximal direction, and the thread 46 of the clip 4 is pulled in the proximal direction by the thread 8 while the knot 461 of the thread 46 of the clip 4 is locked on or abuts against the distal end portion 71 of the fixed tube 7. Further, the deformation portion 42 is locked (indirectly locked) through the knot 461, whereby the knot 461 is moved in the distal direction, the thread 46 is tightened, and the deformation portion 42 is deformed to assume a form as shown in FIG. 20.

As a result of the above, the deformation portion 42 covers the opening and the periphery of the opening from the outside of the blood vessel wall, the seal portion 41 covers the opening and the periphery of the opening from the inside of the blood vessel wall, and the blood vessel wall is sandwiched between the seal portion 41 and the deformation portion 42 so that the opening is closed. The condition in which the deformation portion 42 has come into the above-mentioned form is retained (fixed) by the thread 46.

When the deformation of the deformation portion 42 is completed (when the opening has been closed), the deformation portion 42 cannot be deformed further, the thread 8 is tensioned, and the thread 8 and the thread support portion 15 cannot be moved further and are stopped. However, the cover tube support portion 14 can be moved further in the proximal direction, through contraction of the spring 18. By virtue of the spring 18, the connection between the thread 8 and the thread 46 of the clip 4 is canceled or released, after completion of the deformation of the deformation portion 42 of the clip 4.

More specifically, with the lever 12 of the hand-operated portion 9 turned further, as shown in FIGS. 21 and 22, the cover tube support portion 14 is moved further in the proximal direction while the spring 18 contracts. Then, when the projections 141 of the cover tube support portion 14 are axially moved into contact with the projections 161 of the lifter 16, the projections 161 of the lifter 6 are pushed upward by the projections 141 of the cover tube support portion 14, thus moving the lifter 16 upwards. The upward movement of the lifter 6 causes the pin 17 to be moved upward in the direction which results in the pin 17 coming off the thread support portion 15. As a result, the connection between the thread 8 and the thread support portion 15 by the pin 17 is canceled or released, whereby the connection between the thread 8 and the thread 46 of the clip 4 is canceled or released. Specifically, the turned-back portion 81 of the thread 8 comes off the pin 17, resulting in the thread 8 being pulled out of the ring 462 of the thread 46.

Finally, as shown in FIG. 23, the body portion 2 is evulsed or completely removed, and the clip 4 is disposed in the living body (i.e., the clip 4 is left in the living body).

As described above, the series of operations from the deformation of the deformation portion 42 of the clip 4 to the canceling or releasing of the connection between the thread 8 and the clip 4 (the retained state of the clip 4 by the thread 8) after the completion of the deformation of the deformation portion 42 and the closure of the opening penetrating the living tissue are performed continuously by the operation of the hand-operated portion 9, particularly by the operation of only turning the lever 12. Therefore, the procedure can be easily performed even with one hand, and the staunching work for closing the opening penetrating the living tissue such as the wall of a blood vessel can be performed relatively easily, quickly and reliably. That is, the opening can be closed relatively easily, quickly and assuredly, and with relatively perfect staunching being achieved.

In addition, since the connection between the thread 8 and the clip 4 is canceled or released after the deformation of the deformation portion 42 of the clip 4 is completed, the staunching work can be performed quite safely and reliably.

Also, in the condition where the deformation portion 42 of the clip 4 has been put into a desired form between the first form and the second form, the condition can be maintained by the thread 46. This makes it possible to cope with various conditions (statuses) of the wall of living tissue.

Furthermore, the deformation portion 42 can be deformed quite readily and with relative certainty. This helps ensure that even if defective staunching occurs, the deformation portion 42 would then be in the state of being reliably spread in directions substantially parallel to the seal portion 41, so that staunching by holding down by an individual's hand can thereafter be performed, and the staunching work can be performed quite safely.

While the tissue closing device disclosed herein has been described above by way of the embodiment shown in the drawings, the invention is not limited to the illustrated and described embodiment, and the configuration of various components of the device can be replaced with other features or configurations having the same or equivalent function. Other components may also be added to the disclosed embodiment of the device.

For example, while one of two end portions of the thread 46 is fixed inside the hand-operated portion 9 and the other is subjected to canceling or releasing of the connection in the above-described embodiment, both ends may be simultaneously subjected to canceling or releasing of the connection. In such an alternative, the thread 46 is left on the living body side in the state of being in connection with the clip 4. Thereafter, the thread 46 can be freely evulsed or removed by a procedure conducted by the operator.

The principles and preferred embodiment have been described in the foregoing specification. However, the invention which is intended to be protected is not to be construed as limited to the particular embodiment disclosed. Further, the embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A tissue closing device for closing an opening penetrating living tissue, comprising:
    a closure for closing the opening, the closure comprising a seal portion positionable on one side of the opening in the living tissue to cover the opening and a periphery of the opening, and a deformable deformation portion positionable on an opposite side of the opening in the living tissue;
    a body;
    an elongated tubular member extending distally of the body;
    a thread extending through the elongated tubular member and connected to the closure;
    a manually operable operating lever mounted on the body and operatively connected to the thread by a thread holder to move the thread in a proximal direction upon manual operation of the operating lever so that the thread applies a force to the closure which deforms the deformation portion so that the periphery of the opening penetrating the living tissue is positioned between the seal portion and the deformation portion which has been deformed;
    a release member movably positioned in the body and engageable with the thread holder during manual operation of the operating lever to move the thread holder in a manner which releases the thread and operatively disconnects the thread and the operating lever; and
    wherein the thread holder is a pin supported in a hole in a thread support portion, the release member engaging the pin during manual operation of the operating lever to move the pin out of the hole of the thread support portion.

2. The tissue closing device as set forth in claim 1, further comprising a cover tube support portion movably positioned in the body and connected to the operating lever so that movement of the operating lever causes movement of the cover tube support portion, the cover tube support portion comprising a plurality of projections that engage the release member during operation of the operating lever to move the release member in a manner causing the pin to move out of the hole of the thread support portion.

3. The tissue closing device as set forth in claim 2, further comprising a spring positioned between the thread support portion and the cover tube support portion so that movement of the cover tube support portion causes movement of the thread support portion by way of the spring.

4. The tissue closing device as set forth in claim 2, wherein the release member comprises a frame shaped lifter provided with a plurality of projections that are engaged by the projections on the cover tube support to lift the lifter and move the pin out of the hole of the thread support portion.

5. The tissue closing device as set forth in claim 1, wherein the operative connection between the operating lever and the thread by way of the thread holder comprises a cover tube support portion and a thread support portion which are movable together as a unit by way of a spring positioned between the cover tube support portion and a thread support portion, the cover tube support portion and the thread support portion also being movable relative to one another through contraction of the spring.

6. The tissue closing device as set forth in claim 5, wherein the cover tube support portion supports a cover tube having a distal end portion that initially covers a distal end portion of the elongated tubular member, initial operation of the operating lever causing the cover tube to move in the proximal direction relative to the elongated tubular member so that the distal end portion of the elongated tubular member is exposed distally beyond the distal end portion of the cover tube.

7. A tissue closing device for closing an opening penetrating living tissue, comprising:
    a closure for closing the opening, the closure comprising a seal portion adapted to cover the opening and a periphery of the opening from one side of the wall of the living body cavity, and a deformable deformation portion adapted to cover the opening and the periphery of the opening from an opposite side of the wall of the living body cavity;
    an arrangement device detachably retaining the closure to arrange the closure at a position to close the opening;
    the arrangement device comprising:
        lock means for locking at least a part of the closure in a retained state;
        an operational portion provided on a proximal side of the lock means;
        canceling means for canceling the retained state of the closure; and,
        the operational portion being operable to effect in a continuous operation relative movement between the closure and the lock means under a condition in which the closure is locked by the lock means to deform the deformation portion of the closure, and after completion of the deformation, to cancel the retained state of the closure by the canceling means;
    retaining means for detachably retaining the closure at a distal end portion of the lock means;
    wherein the closure comprises a fixing portion for retaining a condition where the deformation portion has been put into a predetermined form;
    wherein:
    the fixing portion is a thread-like member comprising a movable knot; and
    when the closure is pulled by the retaining means upon operation of the operational portion, the knot is moved on the thread-like member of the fixing portion with the deformation portion being deformed into the predetermined form and retained in the predetermined form by the knot;
    the thread-like member is a first thread-like member, and the retaining means is a second thread-like member different from the first thread-like member, the second thread-like member possessing one end portion and an other end portion, the one end portion of the second thread-like member being detachably connected to a part of the arrangement device, the other end portion of the second thread-like member being un-detachably fixed, the second thread-like member retaining the closure by passing through the closure and being turned back at a distal end portion of the arrangement device; and the one end portion of the second thread-like member includes a loop through which passes a connecting means which is movable from one position in which the connecting means prevents release of the loop to an other position in which the connecting means permits release of the loop.

8. The tissue closing device as set forth in claim 7, wherein the knot is a clinch knot.

9. The tissue closing device as set forth in claim 7, wherein the second thread-like member is connected to the first thread-like member.

10. The tissue closing device as set forth in claim 7, wherein the second thread-like member is connected to the first thread-like member by way of a ring.

11. The tissue closing device as set forth in claim 7, wherein the other end portion of the second thread-like member is fixed to a part of the arrangement device.

12. The tissue closing device as set forth in claim 7, wherein the thread-like member comprises two ends tied together to form the movable knot which is movable relative to the thread-like member to tighten the thread-like member.

13. A tissue closing device for closing an opening penetrating living tissue, comprising:
a closure for closing the opening, the closure comprising a seal portion adapted to cover the opening and a periphery of the opening from one side of the wall of the living body cavity, and a deformable deformation portion adapted to cover the opening and the periphery of the opening from an opposite side of the wall of the living body cavity; and
an arrangement device detachably retaining the closure to arrange the closure at a position to close the opening;
the arrangement device comprising:
lock means for locking at least a part of the closure in a retained state;
an operational portion provided on a proximal side of the lock means;
canceling means for canceling the retained state of the closure; and
the operational portion being operable to effect in a continuous operation relative movement between the closure and the lock means under a condition in which the closure is locked by the lock means to deform the deformation portion of the closure, and after completion of the deformation, to cancel the retained state of the closure by the canceling means;
retaining means for detachably retaining the closure at a distal end portion of the lock means;
wherein the operational portion comprises:
an operational portion body;
a retaining means support portion supporting the retaining means and movable relative to the operational portion body, and
the retaining means support portion being moved in the proximal direction by operation of the operational portion to cause the retaining means to move in the proximal direction and move the closure;
wherein the operational portion comprises connecting means for detachably connecting the retaining means to the retaining means support portion;
after the deformation of the deformation portion of the closure is completed by operation of the operational portion, the connection between the retaining means and the retaining means support portion by the connecting means is released by the canceling means to release the retained state of the closure by the retaining means;

wherein the retaining means is a thread-like member possessing one end portion and an other end portion, the one end portion of the thread-like member being detachably connected to the retaining means support portion by the connecting means, the other end portion of the thread-like member being undetachably fixed, the thread-like member retaining the closure by passing through the closure and being turned back at a distal end portion of the arrangement device;
wherein the canceling means comprises a connecting means support portion supporting the connection means and displaceable relative to the operational portion body;
a displacing portion provided at the cover member support portion and operative to displace the connecting means support portion; and
operation of the operational portion causing the cover member support portion to move in the proximal direction to displace the connecting means support portion by the displacing portion to release the connection means providing connection between the retaining means and the retaining means support portion.

14. The tissue closing device as set forth in claim 13, wherein the arrangement device further comprises:
a cover member covering an outside surface of the lock means and possessing a distal end portion covering at least a part of the closure during positioning of the closure; and
the operation of the operational portion causing the cover member to move in a proximal direction exposing the deformation portion of the closure distally beyond the distal end portion of the cover member before the deformation of the deformation portion.

15. The tissue closing device as set forth in claim 13, wherein during the operation of the operational portion, the retaining means moves the deformation portion of the closure into contact with the distal end portion of the lock means, with further operation of the operational member causing the retaining means to apply a force to the closure locked by the lock means which deforms the deformation portion.

16. The tissue closing device as set forth in claim 13, wherein the lock means is a tubular member having a longitudinally extending passage, and the retaining means passes through the longitudinally extending passage.

17. The tissue closing device as set forth in claim 13, wherein:
the arrangement device further comprises a cover member covering an outside surface of the lock means and possessing a distal end portion covering at least a part of the closure during positioning of the closure;
the operational portion comprising a cover member support portion supporting the cover member and movable together with the cover member, the cover member support portion being movable relative to the operational portion body; and
the operation of the operational portion causing the cover member to move in a proximal direction exposing the deformation portion of the closure distally beyond the distal end portion of the cover member before the deformation of the deformation portion.

18. The tissue closing device as set forth in claim 17, further comprising
an elastic member positioned between the cover member support portion and the retaining means support portion, the elastic member being adapted to be contracted along a moving direction of the cover member support portion and the retaining means support portion; and the movement of the cover member support portion in the proximal direction causing movement of the retaining means support portion in the proximal direction through the elastic member, the movement of the retaining means support portion in response to operation of the operational portion being stopped upon completion of the deformation of the deformation portion of the closure, the elastic member being contracted after deformation of the deformation portion is completed and movement of the retaining means support portion is stopped to permit movement of the cover member support portion relative to the retaining means support portion.

19. The tissue closing device as set forth in claim 13, wherein the canceling means is so configured that connection between the retaining means and the retaining means support portion by the connecting means is canceled by a movement of the cover member support portion in the proximal direction.

20. The tissue closing device as set forth in claim 13, wherein the one end portion of the thread-like includes a loop through which passes the connecting means, the connecting means being movable relative to the retaining means support portion from one position in which the connecting means prevents release of the loop to maintain the retained state of the closure to an other position in which the connecting means permits release of the loop to release the retained state of the closure.

21. The tissue closing device as set forth in claim 13, wherein the closure comprises a fixing portion for retaining a condition where the deformation portion has been put into a predetermined form.

22. The tissue closing device as set forth in claim 21, wherein the retaining means retains the fixing portion of the closure.

23. The tissue closing device as set forth in claim 13, wherein:
    the seal portion is substantially plate-shaped; and
    the deformation portion is in the shape of a frame which is deformable between a first form in which the frame is expanded in a direction substantially perpendicular to the seal portion and is contracted in a direction substantially parallel to the seal portion and a second form in which the frame is contracted in the direction substantially perpendicular to the seal portion and is expanded in the direction substantially parallel to the seal portion.

24. The tissue closing device as set forth in claim 13, wherein the connecting means is movable relative to the retaining means support portion from one position in which the connecting means prevents release of the one end portion of the thread-like member to maintain the retained state of the closure to an other position in which the connecting means permits release of the one end portion of the thread-like member to release the retained state of the closure.

25. The tissue closing device as set forth in claim 13, wherein the other end portion of the thread-like member is fixed to the retaining means support portion.

26. The tissue closing device as set forth in claim 13, wherein the other end portion of the thread-like member is fixed to a part of the arrangement device.

27. The tissue closing device as set forth in claim 13, wherein the lock means is a tube possessing a distal end and a proximal end, the closure being positioned distally of the distal end of the tube, the thread-like member comprising two different portions each positioned in the tube and extending out the proximal end of the tube.

* * * * *